(12) United States Patent
Chance

(10) Patent No.: US 7,627,365 B2
(45) Date of Patent: *Dec. 1, 2009

(54) DETECTION, IMAGING AND CHARACTERIZATION OF BREAST TUMORS

(75) Inventor: Britton Chance, Marathon, FL (US)

(73) Assignee: Non-Invasive Technology Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/983,371

(22) Filed: Nov. 8, 2004

(65) Prior Publication Data

US 2005/0197583 A1    Sep. 8, 2005

Related U.S. Application Data

(63) Continuation of application No. 09/622,184, filed as application No. PCT/US99/02953 on Feb. 11, 1999, now abandoned.

(60) Provisional application No. 60/074,504, filed on Feb. 11, 1998, provisional application No. 60/098,018, filed on Aug. 26, 1998.

(51) Int. Cl.
*A61B 5/00* (2006.01)

(52) U.S. Cl. .................. 600/475; 600/323; 600/328; 600/329; 600/340; 600/431; 600/477; 600/479

(58) Field of Classification Search ............... 600/310, 600/322–324, 326, 328, 329, 340, 431, 473, 600/475–477, 479
See application file for complete search history.

(56) References Cited

U.S. PATENT DOCUMENTS 2,706,927 A    4/1955    Wood ..................... 600/344

(Continued)

FOREIGN PATENT DOCUMENTS

DE    25 38 985    5/1976

(Continued)

OTHER PUBLICATIONS

PCT International Search Report, Int'l Appln. No. PCT/US97/16309, mailed Feb. 10, 1998, 9 pp.

(Continued)

*Primary Examiner*—Ruth S Smith
(74) *Attorney, Agent, or Firm*—Ivan David Zitkovsky

(57) ABSTRACT

An optical examination technique employs an optical system for in vivo non-invasive examination of breast tissue of a subject. The optical system includes an optical module, a controller and a processor. The optical module includes an array of optical input ports and optical detection ports located in a selected geometrical pattern to provide a multiplicity of photon migration paths inside the biological tissue. Each optical input port is constructed to introduce into the examined tissue visible or infrared light emitted from a light source. Each optical detection port is constructed to provide light from the tissue to a light detector. The controller is constructed and arranged to activate one or several light sources and light detectors so that the light detector detects light that has migrated over at least one of the photon migration paths. The processor receives signals corresponding to the detected light and forms at least two data sets, a first of said data sets representing blood volume in the examined tissue region and a second of said data sets representing blood oxygenation of the examined tissue. The processor is arranged to correlate the first and second data sets to detect abnormal tissue in the examined tissue.

52 Claims, 27 Drawing Sheets

U.S. PATENT DOCUMENTS

| | | | |
|---|---|---|---|
| 2,790,438 A | 4/1957 | Taplin et al. | 600/344 |
| 3,068,742 A | 12/1962 | Hicks, Jr. et al. | 600/339 |
| 3,412,729 A | 11/1968 | Smith, Jr. | 600/324 |
| 3,461,856 A | 8/1969 | Polanyl | 600/323 |
| 3,638,640 A | 2/1972 | Shaw | 600/323 |
| 3,704,706 A | 12/1972 | Herezfeld et al. | 600/324 |
| 3,709,612 A | 1/1973 | Clemens | 356/407 |
| 3,866,599 A | 2/1975 | Johnson | 600/342 |
| 3,994,585 A | 11/1976 | Frey | 356/40 |
| 3,998,550 A | 12/1976 | Konishi et al. | 356/39 |
| 4,014,321 A | 3/1977 | March | 600/319 |
| 4,029,085 A | 6/1977 | DeWitt et al. | 600/315 |
| 4,086,915 A | 5/1978 | Kofsky et al. | 600/330 |
| 4,119,406 A | 10/1978 | Clemens | 422/81 |
| 4,129,125 A | 12/1978 | Lester et al. | 600/484 |
| 4,138,727 A | 2/1979 | Mantz | 708/813 |
| 4,162,405 A | 7/1979 | Chance et al. | 424/9.6 |
| 4,167,331 A | 9/1979 | Nielsen | 356/39 |
| 4,222,389 A | 9/1980 | Rubens | 600/328 |
| 4,223,680 A | 9/1980 | Jobsis | 600/324 |
| 4,224,948 A | 9/1980 | Cramer et al. | 600/503 |
| 4,259,963 A | 4/1981 | Huch | 600/359 |
| 4,266,554 A | 5/1981 | Hamaguri | 600/323 |
| 4,281,645 A | 8/1981 | Jobsis | 600/324 |
| 4,321,930 A | 3/1982 | Jobsis et al. | 600/344 |
| 4,380,240 A | 4/1983 | Jobsis et al. | 600/344 |
| 4,416,285 A | 11/1983 | Shaw et al. | 600/339 |
| 4,447,884 A | 5/1984 | Wada | 702/131 |
| 4,452,250 A | 6/1984 | Chance et al. | 600/410 |
| 4,469,107 A | 9/1984 | Asmar et al. | 600/494 |
| 4,510,938 A | 4/1985 | Jobsis et al. | 600/344 |
| 4,515,165 A | 5/1985 | Carroll | 600/475 |
| 4,576,173 A | 3/1986 | Parker et al. | 600/317 |
| 4,612,938 A | 9/1986 | Dietrich et al. | 600/476 |
| 4,648,892 A | 3/1987 | Kittrell et al. | 65/387 |
| 4,655,225 A | 4/1987 | Dahne et al. | 600/316 |
| 4,700,708 A | 10/1987 | New, Jr. et al. | 600/331 |
| 4,714,341 A | 12/1987 | Hamaguri et al. | 356/41 |
| 4,738,267 A | 4/1988 | Lazorthes et al. | 600/561 |
| 4,773,422 A | 9/1988 | Isaacson et al. | 600/326 |
| 4,774,679 A | 9/1988 | Carlin | 702/41 |
| 4,800,495 A | 1/1989 | Smith | 600/322 |
| 4,800,885 A | 1/1989 | Johnson | 600/330 |
| 4,805,623 A | 2/1989 | Jobsis | 600/328 |
| 4,807,637 A | 2/1989 | Bjorkholm | 600/476 |
| 4,824,242 A | 4/1989 | Frick et al. | 356/41 |
| 4,836,207 A | 6/1989 | Bursell et al. | 600/318 |
| 4,846,183 A | 7/1989 | Martin | 600/336 |
| 4,869,254 A | 9/1989 | Stone et al. | 600/336 |
| 4,880,304 A | 11/1989 | Jaeb et al. | 356/41 |
| 4,908,762 A | 3/1990 | Suzuki et al. | 600/407 |
| 4,926,867 A | 5/1990 | Kanda et al. | 600/334 |
| 4,937,526 A | 6/1990 | Ehman et al. | 324/309 |
| 4,940,453 A | 7/1990 | Cadwell | 600/13 |
| 4,951,682 A | 8/1990 | Petre | 600/526 |
| 4,972,331 A | 11/1990 | Chance | 600/310 |
| 5,035,243 A | 7/1991 | Muz | 600/344 |
| 5,057,695 A | 10/1991 | Hirao et al. | 250/575 |
| 5,062,431 A | 11/1991 | Potter | 600/478 |
| 5,088,493 A | 2/1992 | Giannini et al. | 600/323 |
| 5,090,415 A | 2/1992 | Yamashita et al. | 600/324 |
| 5,106,387 A | 4/1992 | Kittrell et al. | 606/15 |
| 5,119,815 A | 6/1992 | Chance | 600/433 |
| 5,122,974 A | 6/1992 | Chance | 600/323 |
| 5,137,355 A | 8/1992 | Barbour et al. | 356/342 |
| 5,139,025 A | 8/1992 | Lewis et al. | 600/477 |
| 5,143,081 A | 9/1992 | Young et al. | 600/554 |
| 5,158,090 A | 10/1992 | Waldman et al. | 600/473 |
| 5,174,298 A | 12/1992 | Dolfi et al. | 600/425 |
| 5,178,142 A | 1/1993 | Harjunmaa et al. | 600/310 |
| 5,187,672 A | 2/1993 | Chance et al. | 600/407 |
| 5,190,039 A | 3/1993 | Takeuchi et al. | 600/311 |
| 5,203,339 A | 4/1993 | Knuttel et al. | 600/425 |
| 5,213,105 A | 5/1993 | Gratton et al. | 600/473 |
| 5,218,962 A | 6/1993 | Mannheimer et al. | 600/331 |
| 5,257,202 A | 10/1993 | Feddersen et al. | 702/32 |
| 5,277,181 A | 1/1994 | Mendelson et al. | 600/322 |
| 5,287,276 A | 2/1994 | Crawford et al. | 378/4 |
| 5,300,097 A | 4/1994 | Lerner et al. | 607/93 |
| 5,309,907 A | 5/1994 | Fang et al. | 600/342 |
| 5,309,912 A | 5/1994 | Knuttel | 600/425 |
| 5,353,799 A | 10/1994 | Chance | 600/473 |
| 5,358,503 A | 10/1994 | Bertwell et al. | 606/27 |
| 5,402,778 A | 4/1995 | Chance | 600/310 |
| 5,408,093 A | 4/1995 | Ito et al. | 250/227.26 |
| 5,413,098 A | 5/1995 | Benaron | 600/310 |
| 5,416,582 A | 5/1995 | Knutson et al. | 356/484 |
| 5,431,170 A | 7/1995 | Mathews | 600/479 |
| 5,494,032 A | 2/1996 | Robinson et al. | 600/323 |
| 5,497,769 A | 3/1996 | Gratton et al. | 600/323 |
| 5,551,422 A | 9/1996 | Simonsen et al. | 600/322 |
| 5,551,423 A | 9/1996 | Sugiura | 600/476 |
| 5,564,417 A * | 10/1996 | Chance | 600/476 |
| 5,596,987 A | 1/1997 | Chance | 600/310 |
| 5,625,458 A | 4/1997 | Alfano et al. | 356/446 |
| 5,655,530 A | 8/1997 | Messerschmidt | 600/366 |
| 5,673,701 A | 10/1997 | Chance | 600/473 |
| 5,704,355 A * | 1/1998 | Bridges | 600/407 |
| 5,706,821 A | 1/1998 | Matcher et al. | 600/310 |
| 5,779,631 A | 7/1998 | Chance | 600/328 |
| 5,782,755 A | 7/1998 | Chance et al. | 600/322 |
| 5,807,263 A | 9/1998 | Chance | 600/476 |
| 5,845,639 A | 12/1998 | Hochman et al. | 600/407 |
| 5,853,370 A | 12/1998 | Chance et al. | 600/473 |
| 5,943,133 A | 8/1999 | Zeylikovich et al. | 356/496 |
| 5,949,077 A | 9/1999 | Alfano et al. | 250/459.1 |
| 5,983,125 A | 11/1999 | Alfano et al. | 600/473 |
| 5,987,351 A | 11/1999 | Chance | 600/473 |
| 6,006,001 A | 12/1999 | Alfano et al. | 385/115 |
| 6,058,324 A | 5/2000 | Chance | 600/473 |
| 6,091,981 A * | 7/2000 | Cundari et al. | 600/407 |
| 6,091,983 A | 7/2000 | Alfano et al. | 600/431 |
| 6,108,576 A | 8/2000 | Alfano et al. | 600/476 |
| 6,119,033 A * | 9/2000 | Spigelman et al. | 600/426 |
| 6,215,587 B1 | 4/2001 | Alfano et al. | 359/368 |

FOREIGN PATENT DOCUMENTS

| | | |
|---|---|---|
| DE | 31 00610 C2 | 1/1981 |
| DE | 208 297 | 6/1982 |
| DE | 43 03 047 A | 8/1994 |
| EP | 0 099 756 | 1/1984 |
| EP | 0 102 816 | 3/1984 |
| EP | 0 290 279 | 9/1985 |
| EP | 0 196 396 | 10/1986 |
| EP | 0 282 234 | 12/1987 |
| EP | 0 488 565 A1 | 6/1992 |
| GB | 2 068 537 | 8/1981 |
| GB | 2 228 314 A | 8/1990 |
| JP | 61 60903 | 4/1966 |
| JP | 59 168834 | 9/1984 |
| JP | 63 61923 | 3/1988 |
| JP | 63 148307 | 9/1988 |
| WO | WO 84/04665 | 12/1984 |
| WO | WO 88/01485 | 3/1988 |
| WO | WO 90/09003 | 8/1990 |
| WO | WO 92/013598 | 8/1992 |
| WO | WO 92/020273 | 11/1992 |
| WO | WO 93/005686 | 12/1993 |
| WO | WO 93/025145 | 12/1993 |
| WO | WO 94/16615 | 4/1994 |
| WO | WO 95/02987 | 2/1995 |

| WO | WO 96/20638 | 7/1996 |
| WO | WO97/20494 | 12/1997 |

OTHER PUBLICATIONS

Apicella et at, "Fast multi-modality image matching", SPIE, vol. 1092, pp. 252-263, 1989.
Arridge, "The Forward and Inverse Problems in Time Resolved Infra-Red Imaging", Medical Optical Tomography: Functional Imaging and Monitoring, SPIE Optical Engineering Press, vol. IS11, pp. 35-64, 1993.
Arridge et al., "Reconstruction Methods for Infra-red Absorption Imaging", SPIE, vol. 1431, pp. 204-215, 1991.
Barlow et al., "Breast Biopsy Analysis By Spectroscopic Imaging", Photon Migration in Tissues, Plenum Press, New York, pp. 111-119, 1989.
Benaron et al., "A Medical Perspective at the Threshold of Clinical Optical Tomography", Medical Optical Tomography: Functional Imaging and Monitoring. SPIE Optical Engineering Press, vol. IS11, pp. 3-9, 1993.
Bonner et al., "Model for photon migration in turbid biological media", J. Opt. Soc. Am. A., vol. 4, No. 3, pp. 423-427, 1987.
Chance, "The Future of Time Resolved Spectroscopy and Imaging", Proceedings of The Third International Conference: Peace through Mind/Brain Science, pp. 166-172, Aug. 5-10, 1990, Hamamatsu, Japan.
Chance et al., "Time Resolved Spectroscopy of Hemoglobin and Myoglobin in Resting and Ischemic Muscle", Anal. Biochem. 174:698-707, 1988.
Chance et al, "Photon Migration in Muscle and Brain", Photon Migration in Tissues, Plenum Press, New York, pp. 121-135, 1989.
Chance et al, "Rapid and Sensitive Spectrophotometry. I. The Accelerated and Stopped-Flow Methods for the Measurement of the Reaction Kinetics and Spectra of Unstable-Compounds in the Visible Region of the Spectrum", The Review of Scientific Instruments, vol. 22, pp. 619-627, 1951.
Chance et al., "Rapid and Sensitive Spectrophotometry. Il. A Stopped-Flow Attachment for a Stabilized Quartz Spectrophotometer", The Review of Scientific Instruments, vol. 22, pp. 627-638, 1951.
Chance et al., "Comparison of time-resolved and —unresolved measurements of deoxyhemoglobin in brain", Proc. Natl. Acad. Sci. USA., vol. 85, pp. 4971-4975, 1988.
Colak at al, "Optical BackProjection Tomography in Heterogeneous Diffusive Media", Advances in Optical Imaging and Photon Migration, TOPS, vol. 2, pp. 282-289, 1996.
Cui et al, "Experimental Study of Migration Depth for the Photons Measured At Sample Surface", SPIE, vol. 1431, pp. 180-191, 1991.
Feng et al., "Analytical perturbation theory of photon migration in the presence of a single absorbing or scattering defect sphere", SPIE, vol. 2389, pp. 54-63, 1995.
Fishkin et al., "Diffusion of Intensity Modulated Near-Infrared Light in Turbid Media", SPIE, vol. 1431, pp. 122-135, 1991.
Gratton at al., "The Possibility of a Near Infrared Optical Imaging System Using Frequency Domain Methods", Mind Brain Imaging Program, Aug. 5-10, 1990, Hamamatsu, Japan.
Grübaurn et al., "Diffuse Tomography", SPIE, vol. 1431, pp. 232-238, 1991.
Greenfeld, "A Tissue Model for Investigating Photon Migration in Trans-Cranial Infrared Imaging", Photon Migration in Tissues, Plenum Press (New York), pp. 147-168, 1989.
Grinvald et al., "Functional Architecture of Cortex Revealed by Optical Imaging of Intrinsic Signals", Nature, 324:361-364, 1986.

Haida et al., "A Method to Estimate the Ratio of Absorption Coefficients of Two Wavelengths Using Phase Modulated NIR Spectroscopy", abstract submitted to ISOTT in Mainz. Germany, 1992.
Haide et al., "A Method to Estimate the Ratio of Absorption Coefficients of Two Wavelengths Using Phase Modulated Near Infrared Light Spectroscopy", Oxygen Transport to Tissue XV, Plenum Press, New York, vol. 345, pp. 829-835, 1994.
Haida et al., "A Method to Estimate the Ratio of Absorption Coefficients of Two Wavelengths Using Phase-Modulated Near Infrared Light Spectroscopy", Analytical Biochemistry, vol. 208, pp. 348-351, 1993.
Hajnal et al., "Artifacts Due to Stimulus Correlated Motion in Functional Imaging of the Brain", MRM, pp. 283-291, 1994.
Hoshi et al., "Detection of dynamic changes in cerebral oxygenation coupled to neuronal function during mental work in man", Neuroscience Letters, vol. 150, pp. 5-8, 1993.
Maki et al., "Spatial and temporal analysis of human motor activity using noninvasive NIR topography", Med. Phys., vol. 22, No. 12, pp. 1997-2005, 1995.
Matcher et al., "Absolute quantification methods in tissue near infrared spectroscopy", SPIE, vol. 2389, pp. 486-495, 1995.
Nioka et al, "Optical Imaging of Breast Tumors with various methods", Oxygen Transport to Tissue, vol. XVIII, pp. 227-232, 1997.
Oda et al., "Non-Invasive Hemoglobin Oxygenation Monitor and Computered Tomography by NIR Spectrophotometry", SPIE 1431:284-293, 1991.
Ogawa et el., "The Sensitivity of Magnetic Resonance Image Signals of a Rat Brain to Changes in the Cerebral Venous Blood Oxygenation", MRM, vol. 29, pp. 205-210, 1993.
Pelizzari et al., "Accurate Three-Dimensional Registration of CT, PET, and/or MR Images of the Brain", J. Computer-Assisted Tomography, vol. 13, No. 1, pp. 20-26, 1989.
Polishchuk et al., "Non-Euclidean diffusion and 'Format' photons in turbid media", SPIE, vol. 2389, pp. 6-9, 1995.
Sevick et al., "The physical basis of biomedical optical imaging using time-dependent measurements of photon migration in the frequency domain", Medical Optical Tomography: Functional Imaging and Monitoring, SPIE Optical Engineering Press, vol. IS11, pp. 483-512, 1993.
Sevick et al., "Analysis of Absorption, Scattering and Hemoglobin Saturation Using Phase Modulation Spectroscopy", SPIE vol. 1431, pp. 264-275, 1991.
Sevick at al., "Photon Migration in a Model of the Head Measured Using Time- and Frequency- Domain Techniques Potentials of Spectroscopy and Imaging", SPIE, vol. 1431, pp. 84-96, 1991.
Sevick at al., "Quantitation of Time-and Frequency-Resolved Optical Spectra for the Determination of Tissue Oxygenation," Analytical Biochemistry, vol. 195, pp. 330-351, 1991.
Singer at al., "Image Reconstruction of the Interior of Bodies that Diffuse Radiation", Science, vol. 248, pp. 990-993, 1990.
Weng at al, "Measurement of Biological Tissue Metabolism Using Phase Modulation Spectroscopy Technology," SPIE, 1431:161-171, 1991.
Woods et al., "Rapid Automated Algorithm for Aligning and Reslicing PET Images", J. Computer Assisted Tomography , vol. 16, No. 4, pp. 620-633, 1992.
Yamashita et al., "The Neonate Brain (NIR) and Breast Imaging Using Transillumination", Photon Migration in Tissues, Plenum Press, New York, pp. 55-67, 1989.
Brochure, Becton Dickinson, Cardio-Greene® (CG®) HW&D Brand of Sterile Indocyanine Green, USP, Apr. 1981.
"Watching The Brain At Work", IEEE, Spectrum, vol. 20, No. 3, pp. 52-57, 1983.

* cited by examiner

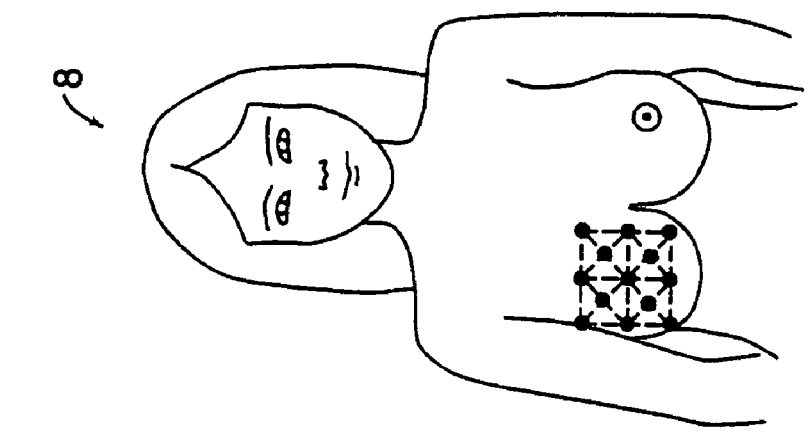
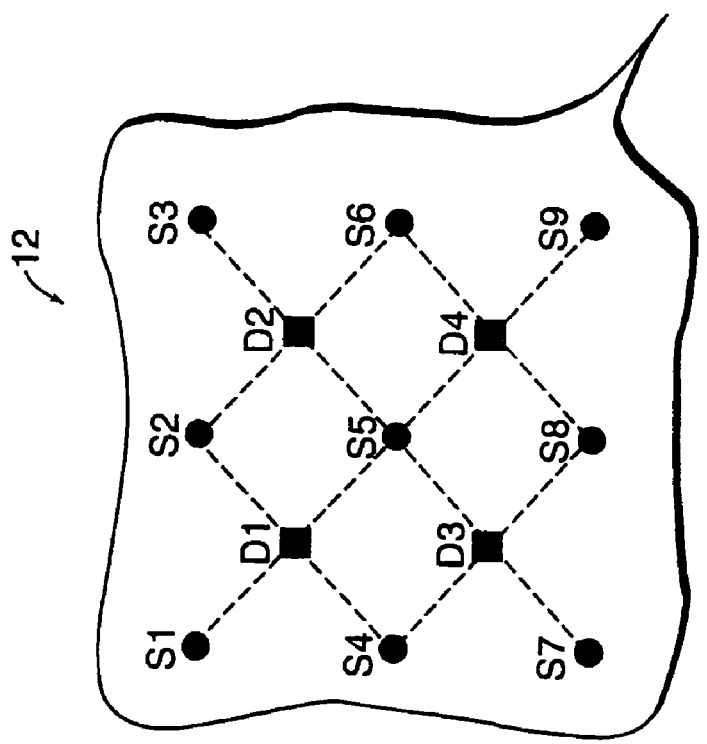
FIG. 1
FIG. 1A

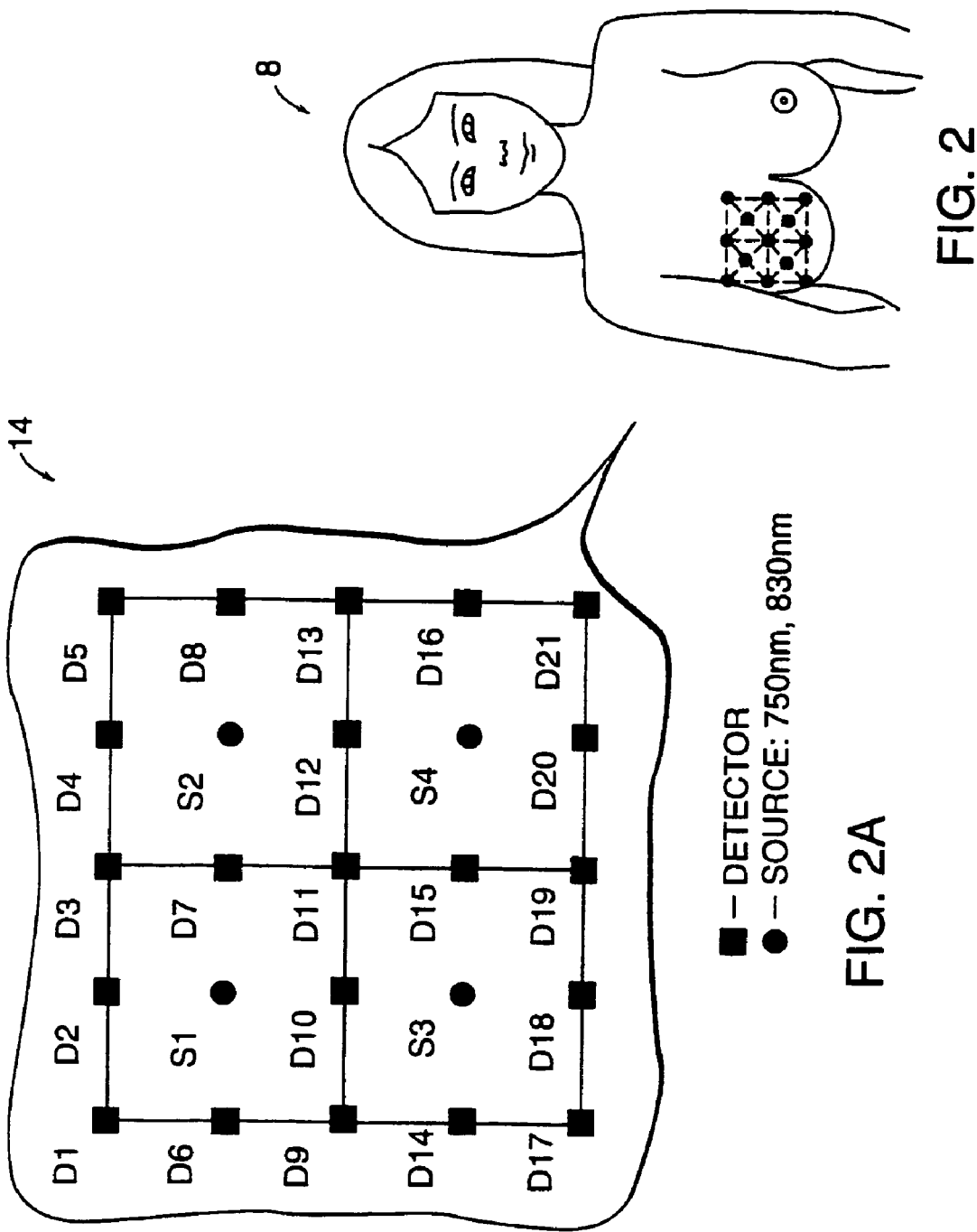

| SOURCES | DETECTORS |
|---|---|
| 1, 2, 1a AND 2a | 1 |
| 2, 3, 2a, AND 3a | 2 |
| 4, 5, 4a, AND 5a | 1 |
| 5, 6, 5a, AND 4a | 2 |
| 7, 8, 7a, AND 8a | 3 |
| 8, 9, 8a, AND 9a | 4 |
| 4, 5, 4a, AND 5a | 3 |
| 5, 6, 5a, AND 6a | 4 |
| 7, 8, 7a, AND 8a | 3 |

HOMODYNE PHASE CANCELLATION IMAGER
(ONE 2S ID PART OF IMAGER)

AMPLITUDE CANCELLATION SYSTEM HUMAN BREAST TEST
RIGHT BREAST — MODEL (ER 11/26/97)

750 nm 830 nm 750 nm − 830 nm 0.3 × 750 nm + 830 nm

SNH 38

AMPLITUDE CANCELLATION SYSTEM HUMAN BREAST TEST
RIGHT BREAST — LEFT BREAST (ER 11/26/97)
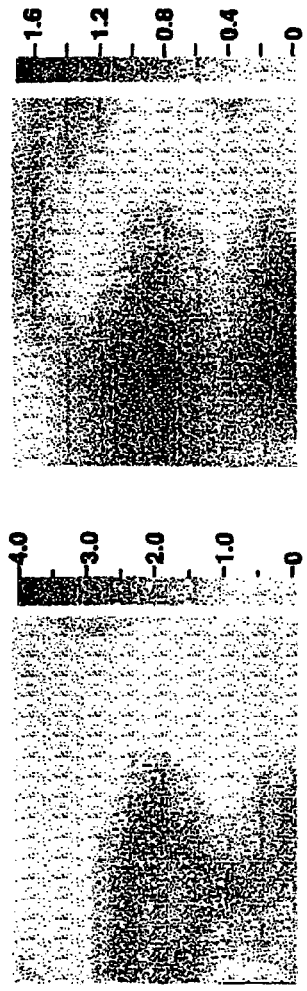
750 nm
FIG. 11A
830 nm
FIG. 11B
750 nm − 830 nm
FIG. 11C
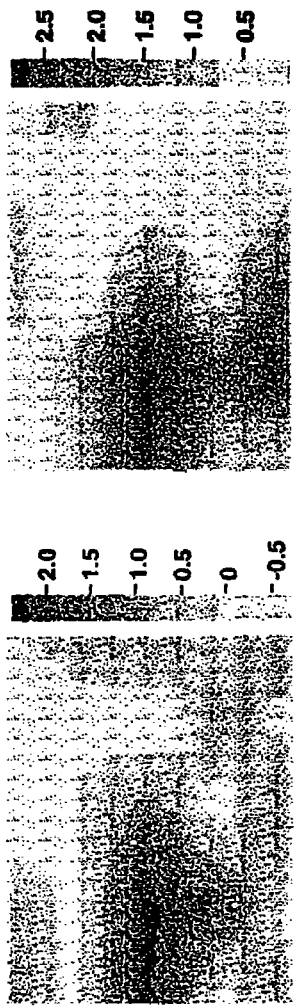
0.3 × 750 nm + 830 nm
FIG. 11D
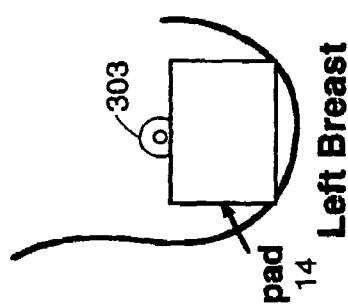
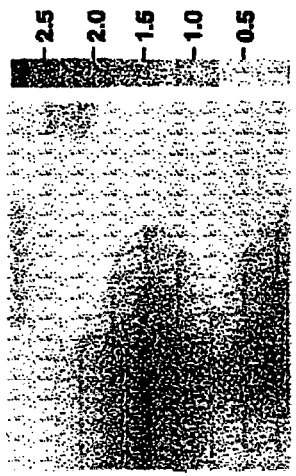
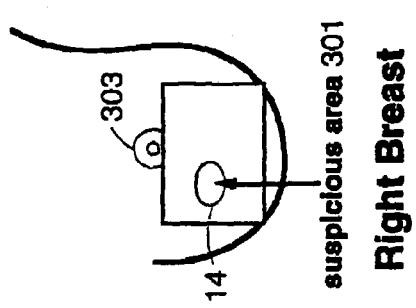

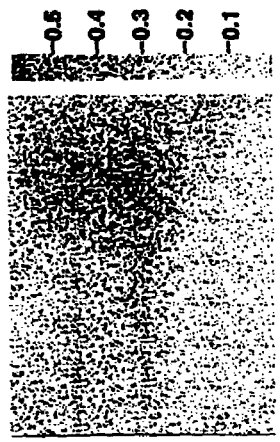
FIG. 12B
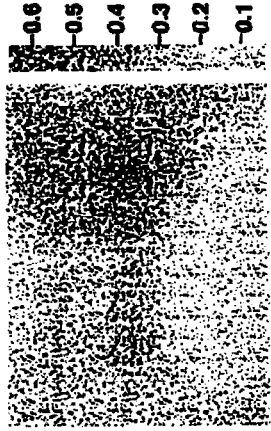
FIG. 12D
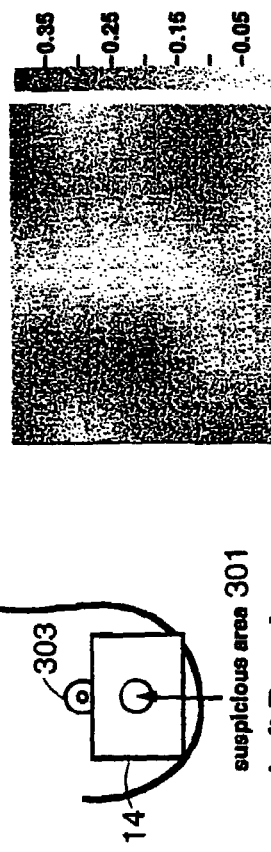
FIG. 12A
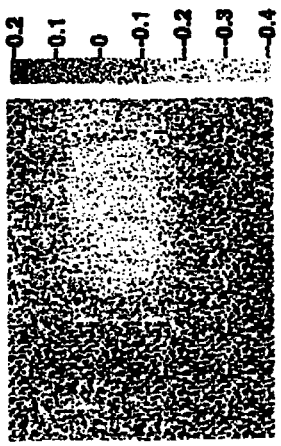
FIG. 12C
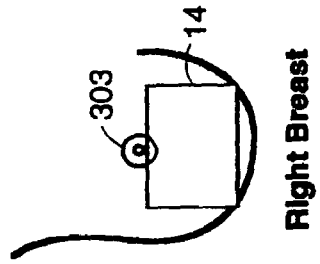

AMPLITUDE CANCELLATION SYSTEM HUMAN BREAST TEST
RIGHT BREAST — MODER (JR 11/26/97)

750 nm 830 nm 750 nm − 830 nm 0.3 × 750 nm + 830 nm

DETECTION, IMAGING AND CHARACTERIZATION OF BREAST TUMORS

This application is a continuation of U.S. application Ser. No. 09/622,184 filed on Jan. 24, 2001, now abandoned which is a 371 of PCT/US99/02953, filed Feb. 11, 1999, which claims priority from U.S. Provisional Application Ser. No. 60/074,504 filed on Feb. 11, 1998 and from U.S. Provisional Application Ser. No. 60/098,018 filed on Aug. 26, 1998, all of which are incorporated by reference as if fully set forth herein.

THE FIELD OF THE INVENTION

The present invention relates to imaging and qualitative or quantitative characterization of biological tissue using visible or infra-red radiation, and more particularly to detection, imaging and characterization of breast tumors.

BACKGROUND

Traditionally, potentially harmful ionizing radiation (for example X-ray or γ-ray) has been used to image biological tissue. This radiation propagates in the tissue on straight, ballistic tracks, i.e., scattering of the radiation is negligible. Thus, imaging is based on evaluation of the absorption levels of different tissue types. For example, in roentgenography the X-ray film contains darker and lighter spots. In more complicated systems, such as computerized tomography (CT), a cross-sectional picture of human organs is created by transmitting X-ray radiation through a section of the human body at different angles and by electronically detecting the variation in X-ray transmission. The detected intensity information is digitally stored in a computer which reconstructs the X-ray absorption of the tissue at a multiplicity of points located in one cross-sectional plane.

Near infra-red radiation (NIR) has been used to study non-invasively the oxygen metabolism in tissue (for example, the brain, finger, or ear lobe). Using visible, NIR and infra-red (IR) radiation for medical imaging could bring several advantages. In the NIR or IR range the contrast factor between a tumor and a tissue is much larger than in the X-ray range. In addition, the visible to IR radiation is preferred over the X-ray radiation since it is non-ionizing and thus, potentially causes fewer side effects. However, the visible or IR radiation is strongly scattered and absorbed in biological tissue, and the migration path cannot be approximated by a straight line, making inapplicable certain aspects of cross-sectional imaging techniques.

Computerized Tomography using NIR spectrometry has been used for in vivo imaging. This technique utilizes NIR radiation in an analogous way to the use of X-ray radiation in an X-ray CT. The X-ray source is replaced by several laser diodes emitting light in the NIR range. The NIR-CT uses a set of photodetectors that detect the light of the laser diodes transmitted through the imaged tissue. The detected data are manipulated by a computer similarly as the detected X-ray data would be in an X-ray CT. Different NIR-CT systems have recognized the scattering aspect of the non-ionizing radiation and have modified the X-ray CT algorithms accordingly.

The above-mentioned X-ray or γ-ray techniques have been used to detect a tissue tumor. Under the term "angiogenesis" I mean the generation of new blood vessels into a tissue or organ. Under normal physiological conditions humans or animals undergo angiogenesis only in very specific restricted situations. For example, angiogenesis is normally observed in wound healing, fetal and embryonal development and formation of the corpus luteum, endometrium and placenta.

Both controlled and uncontrolled angiogenesis are thought to proceed in a similar manner. Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic dependent or angiogenic associated diseases. The hypothesis that tumor growth is angiogenesis dependent was first proposed in 1971. (Folkman J., Tumor angiogenesis: Therapeutic implications, N. Engl. Jour. Med. 285: 1182-1186, 1971) In its simplest terms it states: "Once tumor 'take' has occurred, every increase in tumor cell population must be preceded by an increase in new capillaries converging on the tumor." Tumor 'take' is understood to indicate a prevascular phase of tumor growth in which a population of tumor cells occupying a few cubic millimeters volume and not exceeding a few million cells, can survive on existing host microvessels. Expansion of tumor volume beyond this phase requires the induction of new capillary blood vessels. This explanation was directly or indirectly observed and documented in numerous publications.

Breast cancer is among the most common and the most feared malignancies in women. It has an unpredictable course, the treatment is frequently physically and emotionally draining and the risk of metastatic spread persists for many years. Due to its high occurrence rate, routine breast cancer screening, which includes physical examination and x-ray mammography, plays an important role in current health care. X-ray mammography can detect perhaps 90% of all masses and increases the 10-year survival rate to about 95% for patients with cancers solely detected by mammography. Although the modern mammography uses a low-dose of x-rays, it still involves some very small risk of inducing cancers by the radiation. Other tests, such as magnetic resonance imaging (MRI) and gadolinium enhanced MRI, have been used successfully for detection of breast tumors and may be used routinely for screening in the future.

After a small suspicious mass is detected in the breast non-invasively, an excisional biopsy is usually performed to exclude or diagnose malignancy. The biopsy specimen is removed under local anesthesia and is used for histopathological diagnosis. The statistics show that up to 75% of the excisional biopsies, the biopsied tissue is diagnosed to be benign. Thus, a majority of patients undergoes this unpleasant and costly procedure unnecessarily.

Therefore, a non-invasive, relatively inexpensive technique that can detect and characterize breast tumors may find its place in today's health care alone or in conjunction with the above-mentioned techniques.

SUMMARY

The present invention includes different novel apparatuses and methods for optical examination of biological tissue, in general, and breast tissue, specifically, using visible or infra-red light. The optical examination technique can be used alone to detect and characterize a breast tumor, or can be used in combination with X-ray mammography, ultrasound examination, fMRI, or a needle biopsy. Furthermore, the optical examination technique can be used to examine women of any age.

The technique can employ one or several optical modules positioned on the right or left breast of a female patient placed in different positions. The patient may be sitting upright supporting the examined breast by the optical module, or may be lying face down with the breast on the optical module pad. Alternatively, the patient may be lying supine face up with the breast spread over the chest as evenly as possible. If a suspicious mass is detected, the technique can non-invasively characterize the mass by taking optical data at different wavelengths and by measuring one or several tissue specific characteristics related to the tissue metabolism (or hypermetabolism), biochemistry, pathophysiology (including angiogenesis) or another characteristic of a pathological tissue condition.

In one aspect, the optical examination technique employs an optical system for in vivo non-invasive examination of a volume of biological tissue of a subject. The optical examination system includes an optical module, a controller and a processor. The optical module includes an array of optical input ports and optical detection ports located in a selected geometrical pattern to provide a multiplicity of source-detector paths of photon migration inside the biological tissue. Each optical input port is constructed to introduce into the tissue volume visible or infrared light emitted from a light source. Each optical detection port is constructed to provide light from the tissue to a light detector. The controller is constructed and arranged to activate one or several light sources and light detectors so that the light detector detects light that has migrated over at least one of the source-detector migration paths. The processor receives signals corresponding to the detected light and creates a defined spatial image of the examined tissue.

The optical examination system may generate single wavelength or multiple wavelength images of the examined tissue, wherein the employed wavelength is sensitive to absorption or scattering by a tissue constituent (e.g., an endogenous or exogenous pigment, tissue cells, chemical compounds) or is sensitive to structural changes in the tissue. The optical images may display tissue absorption, tissue scattering, or both. The optical imaging system may also generate blood volume hemoglobin oxygenation images and hemoglobin deoxygenation images (or images of any other tissue constituent) based on a single wavelength optical data or a multiple wavelength optical data. A processor may use different image processing and enhancing algorithms known in the art. The processor may correlate several images taken on the same tissue or taken on symmetrical tissue regions such as the left breast and the right breast, or the left arm and the right arm. Based on this correlation, the system detects a suspicious tissue mass and characterize the detected mass. The correlation includes determining congruency of the structures detected in different images. The processor may employ different types of combined scoring, based on several optical images alone or in combination with X-ray mammography, ultrasound examination, or fMRI, to characterize a suspicious tissue mass.

The optical imaging system may generate the above-described images by examining symmetrical tissue regions of the right breast and the left breast, or may generate images of both the entire right breast and the entire left breast. To identify and characterize a suspicious tissue mass, the processor may employ the different types of combined scoring by correlating the right breast image with the left breast image.

The optical imaging system may collect single wavelength or multiple wavelength data of a breast tissue model for calibration or for detection of background data. In the calibration procedure, the optical module is placed on the model, and the imaging system can collect a limited number of optical data or can collect optical data using the same sequences as used during the tissue examination. The system may either collect and store the model data for subsequent digital processing, or may adjust the source or detector gains to detect optical data according to a predetermined optical pattern. The imaging system may use different breast models having the same scattering coefficient and the same absorption coefficient as the normal breast tissue of a female, for example, below 40 years or above 40 years. Furthermore, the models may have different sizes and have a shape of a female breast during examination. For example, the model has a shape of the breast (or the breast and a portion of the chest) of a woman lying on her back during examination.

According to another aspect, the optical examination technique employs an optical system for in vivo, non-invasive examination of biological tissue of a subject. The optical system includes an optical module, a controller, and a processor. The optical module includes an array of optical input ports and detection ports located in a selected geometrical pattern to provide a multiplicity of photon migration paths inside an examined region of the biological tissue. Each optical input port is constructed to introduce visible or infrared light emitted from a light source. Each optical detection port is constructed to receive photons of light that have migrated in the examined tissue region from at least one of the input ports and provide the received light to a light detector. The controller is constructed and arranged to control operation of the light source and the light detector to detect light that has migrated over at least one of the photon migration paths. The processor is connected to receive signals from the detector and arranged to form at least two data sets, a first of the data sets representing blood volume in the examined tissue region and a second of the data sets representing blood oxygenation in the examined tissue region. The processor is arranged to correlate the first and second data sets to detect abnormal tissue in the examined tissue region.

Preferably, the second data set includes hemoglobin deoxygenation values. The processor may be arranged to form a third data set being collected by irradiating a reference tissue region.

According to another aspect, the optical examination technique employs an optical system for in vivo, non-invasive examination of biological tissue of a subject. The optical system includes an optical module, a controller, and a processor. The optical module includes an array of optical input ports and detection ports located in a selected geometrical pattern to provide a multiplicity of photon migration paths inside an examined region of the biological tissue. Each optical input port is constructed to introduce visible or infrared light emitted from a light source. Each optical detection port is constructed to receive photons of light that have migrated in the tissue from at least one of the input ports and provide the received light to a light detector. The controller is constructed and arranged to control operation of the light source and the light detector to detect light that has migrated over at least one of the photon migration paths. The processor is connected to receive signals from the detector and arranged to form at least two data sets, a first of the data sets being collected by irradiating an examined tissue region of interest and a second of the data sets being collected by irradiating a reference tissue region having similar light scattering and absorptive properties as the examined tissue region. The processor is arranged to correlate the first and second data sets to detect abnormal tissue in the examined tissue region.

According to another aspect, the optical examination technique employs an optical system for in vivo, non-invasive examination of biological tissue of a subject. The optical system includes an optical module, a controller, and a processor. The optical module includes an array of optical input ports and detection ports located in a selected geometrical pattern to provide a multiplicity of photon migration paths inside an examined region of the biological tissue or a model representing biological tissue. Each optical input port is constructed to introduce visible or infrared light emitted from a light source. Each the optical detection port is constructed to receive photons of light that have migrated in the tissue or the model from at least one of the input ports and provide the received light to a light detector. The controller is constructed and arranged to control operation of the light source and the light detector to detect light that has migrated over at least one of the photon migration paths. The processor is connected to receive signals from the detector and arranged to form at least two data sets of two tissue regions, a first of the data sets being collected by irradiating an examined tissue region and a second of the data sets being collected by irradiating a region of a tissue model having selected light scattering and absorptive properties. The processor is arranged to correlate the first and second data sets to detect abnormal tissue in the examined tissue region.

Preferred embodiments of these aspects of the inventions have one or more of the following features.

The processor may be arranged to correlate the first and second data sets by determining congruence between data of the two sets.

The processor may be programmed to order the first and second data sets as two-dimensional images and to determine the congruence using the two-dimensional images. The processor may be programmed to order the first and second data sets as two-dimensional images and to determine the congruence using the following formula:

$$1 - \left(\frac{\text{maximum overlap residual}}{\text{maximum selected tissue signal}}\right) \times 100$$

The processor may be further arranged to determine a location of the abnormal tissue within the examined tissue region.

The processor may be adapted to produce from the data set an image data set by implementing an optical tomography algorithm. The optical tomography algorithm may use factors related to determined probability distribution of photons attributable to the scattering character of the tissue being imaged.

The controller may be arranged to activate the source and the detector to obtain a first selected distance between the input and detection ports, and the processor may be arranged to form the data set for the first distance. The processor may produce an image data set from the data set formed for the first distance. The controller may further be arranged to activate the source and the detector to obtain a second selected distance between the input and detection ports and is arranged to form another data set for the second distance.

The optical system may further include a display device constructed to receive the image data set from the processor and to display an image.

The optical system may further include a first oscillator and a phase detector. The first oscillator is constructed to generate a first carrier waveform at a first frequency on the order of $10^8$ Hz, the first frequency having a time characteristic compatible with the time delay of photon migration from the input port to the detection port. The light source is coupled to the first oscillator and constructed to generate the light modulated by the first carrier waveform. The phase detector is constructed to determine change in waveform of the detected light relative to the waveform of the introduced light and measure therefrom the phase shift of the detected light at the wavelength, wherein the phase-shifted light is indicative of scattering or absorptive properties of the examined tissue region. The processor is arranged to form the data set based on the measured phase shift. This optical system may further include a second oscillator constructed to generate a second waveform at a second frequency. The detector is then arranged to receive a reference waveform at a reference frequency offset by a frequency on the order of $10^3$ Hz from the first frequency and to produce a signal, at the offset frequency, corresponding to the detected radiation. The phase detector is adapted to compare, at the offset frequency, the detected radiation with the introduced radiation and to determine therefrom the phase shift.

The optical system may further include an oscillator, a phase splitter, and first and second double balanced mixers. The oscillator is constructed to generate a first carrier waveform of a selected frequency compatible with time delay of photon migration from the input port to the detection port The light source is connected to receive from the oscillator the carrier waveform and is constructed to generate optical radiation modulated at the frequency. The phase splitter is connected to receive the carrier waveform from the oscillator and produce first and second reference phase signals of predefined substantially different phases. The first and second double balanced mixers are connected to receive from the phase splitter the first and second reference phase signals, respectively, and are connected to receive from the detector the detector signal and to produce therefrom a in-phase output signal and a quadrature output signal, respectively. The processor being connected to the double balanced mixers and arranged to receive the in-phase output signal and the quadrature output signal and form therefrom the data set.

The processor may be arranged to calculate a phase shift ($\Theta_\lambda$) between the light introduced at the input port and the light detected at the detection port prior to forming the data set.

The processor may arranged to calculate an average migration pathlength of photons scattered in the examined tissue between the optical input port and the optical detection port prior to forming the data set.

The processor may further employ the pathlength in quantifying hemoglobin saturation (Y) of the examined tissue.

The processor may be arranged to calculate a signal amplitude ($A_\lambda$) determined as a square root of a sum of squares of the in-phase output signal and the quadrature output signal prior to forming the data set.

The optical system may further include a narrow band detector connected to receive from the optical detector the detector signal and to produce a DC output signal therefrom. The processor then further determines a modulation index ($M_\lambda$) as a ratio of values of the signal amplitude and the signal amplitude plus the DC output signal.

The optical system may further include at least one oscillator connected to at least one light source. The oscillator is constructed to generate a carrier waveform of a selected frequency. The light source generate slight of a visible or infrared wavelength being intensity modulated at the frequency to achieve a known light pattern. The controller is constructed to control the emitted light intensity or phase relationship of patterns simultaneously introduced from multiple input ports, wherein the introduced patterns form resulting radiation that possesses a substantial gradient of photon density in at least one direction. This resulting radiation is scattered and absorbed over the migration paths. The detector is constructed and arranged to detect over time the resulting radiation that has migrated in the tissue to the detection port. The processor is further arranged to process signals of the detected resulting radiation in relation to the introduced radiation to create the data sets indicative of influence of the examined tissue upon the substantial gradient of photon density of the resulting radiation.

The optical system may further include a phase detector constructed to detect the phase of the detected radiation and provide the phase to the processor.

The optical system may further include an amplitude detector constructed to detect the amplitude of the detected radiation and provide the amplitude to the processor.

The phase relationship of light patterns introduced from two input ports may be 180 degrees.

The optical system may be constructed as described in U.S. Pat. Nos. 5,119,815 or 5,386,827. This system includes a light source constructed to generate pulses of radiation of the wavelength, the pulses having a known pulse wave form of a duration on the order of a nanosecond or less. An optical detector is constructed to detect over time photons of modified pulses that have migrated in the tissue from the input ports. This system also includes an analyzer connected to the detector and adapted to determine a change in the pulse waveform shape of the detected pulses relative to the introduced pulses, at the employed wavelength. The processor then creates the data set based on the determined pulse waveform change. The processor may also be constructed and arranged to calculate the effective pathlength of photons of the wavelength migrating between the input and detection ports in conjunction with creating the data set. The processor may also be constructed and arranged to calculate the scattering coefficient at the wavelength in conjunction with creating the image data set The processor may also be constructed and arranged to calculate the absorption coefficient at the wavelength in conjunction with creating the data set.

The optical system may use the light source that produces relatively long light pulses and the processor that forms the data set by subtracting amplitude of two the pulses emitted from two input ports located symmetrically relative to one detection port.

The optical system may be constructed to introduce and detect photons at two wavelengths selected to be sensitive to a tissue constituent. The tissue constituent may be an endogenous pigment or an exogenous pigment. The endogenous pigment may be hemoglobin. The exogenous pigment may be a selected contrast agent.

Other advantages and features of the invention will be apparent from the following description of the preferred embodiment and from the claims.

BRIEF DESCRIPTION OF THE DRAWINGS

FIGS. 1 and 1A show an optical module located on the right breast of a female subject.

FIGS. 2 and 2A show another embodiment of the optical module located on the right breast of the female subject.

FIG. 3B is a timing diagram used by the imaging system of FIGS. 3 and 3A.

FIGS. 10A, 10B, 10C, 10D, 11A, 11B, 11C, 11D, 12A, 12B, 12C, 12D, 13A, 13B, 13C, and 13D are back-projection images of breast tissue collected by the amplitude cancellation system of FIG. 8

DESCRIPTION OF THE PREFERRED EMBODIMENTS

Figure 1B:
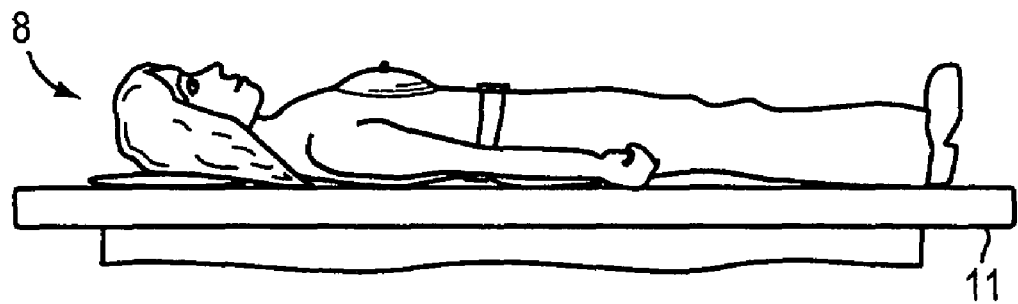
FIGS. 1B and 1C are a side view and a top view of a female subject lying supine, face up and having an optical module located on the right breast.

Referring to FIGS. 1, 1A, 2 and 2A the right breast and the left breast of a female subject 8 are examined using an imaging system connected to an optical module 12 or 14. Optical modules 12 and 14 include a multiplicity of light sources (e.g., laser diodes, LEDs, flashlight bulbs) providing light in the visible to infrared range and light detectors (e.g., photomultiplier tubes, Si diode detector, PIN, avalanche or other diode detectors), which may also include interference filters. The light sources and the light detectors are arranged to form selected geometrical patterns that provide a multiplicity of source-detector paths of photon migration inside the breast tissue. An optical examination system provides an in vivo optical data of the examined tissue, and the data may be processed to create an image. The image can show a location and size of an abnormal structure in the tissue, such as a tumor or bleeding. Furthermore, the optical data can provide a qualitative and quantitative measure (e.g., metabolic biochemistry, pathophysiology) of an abnormal tissue structure. (Alternatively, an optical module includes a multiplicity of optical fibers connected to one or several light sources and a multiplicity of optical detection fibers connected to one or several light detectors as described in the PCT Applications PCT/US96/00235 and PCT/US96/11630 (filed Jan. 2, 1996 and Jul. 12, 1996).)

In one embodiment, optical module 12 includes nine laser diodes $S_1, S_2, \ldots, S_9$ and four photomultiplier tubes (PMTs) $D_1, D_2, D_3, D_4$. The laser diodes and PMTs are embedded in a pliable rubber-like material positioned in contact with the examined breast. There may be a Saran® wrap or similar material located between the laser diodes and the skin, and between the PMTs and the skin. Similarly, optical module 14 includes four laser diodes $S_1, S_2, S_3, S_4$ and 27 silicon diode detectors $D_1, D_2, \ldots, D_{27}$ embedded in a pliable rubber-like material. The optical systems shown in FIGS. 3 through 7 may be interfaced with optical module 12 or 14 for imaging of the breast tissue. Optical modules 12 and 14 have pairs of optical input ports symmetrically located (or equidistantly located) relative to an optical detection port, or have pairs of optical detection ports symmetrically located relative to an optical input port. In general, however, the ports do not have to be positioned symmetrically. The optical systems can vary the source or detector gain to account for any positional asymmetry or can introduce a selected asymmetry by adjusting the source or detector gain.

Furthermore, the optical systems shown in FIGS. 3 through 7, may be interfaced with two identical optical modules (12 or 14) located on the right breast and the left breast for lateralization, that is, comparative examination of the symmetric parts of the right breast and the left breast. For calibration, the optical module may also be placed on one or several breast models having the same scattering coefficient and the same absorption coefficient as the normal breast tissue of a female, for example, below 40 years and above 40 years, and having different sizes and geometries. Alternatively, the breast tissue models may have other selected values of the scattering and absorption coefficient.

Figure 3:
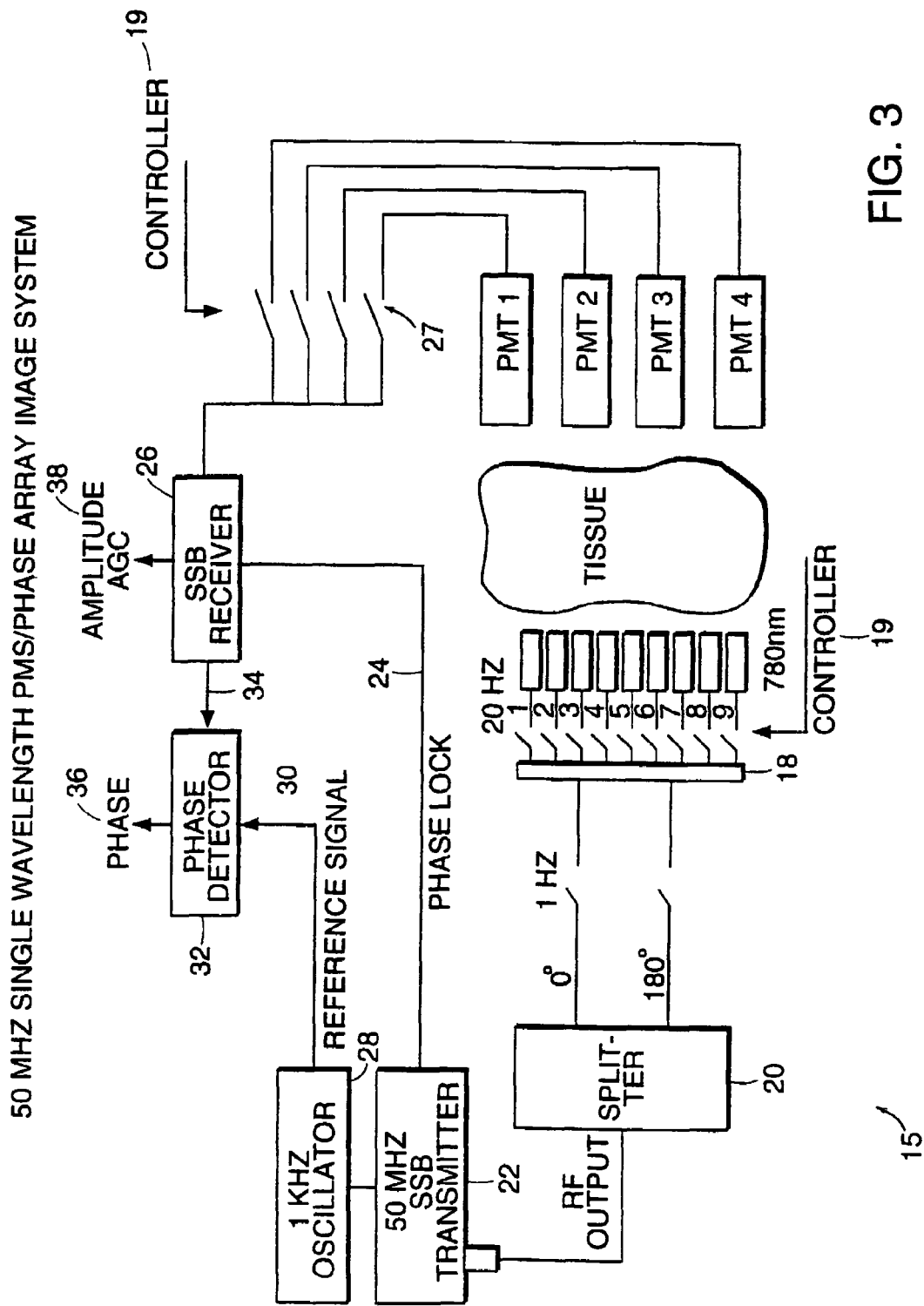
FIGS. 3 and 3A show diagrammatically respective single wavelength and dual wavelength phase cancellation imaging systems that employ the optical module of FIG. 1A or FIG. 2A.

Referring to FIGS. 1A and 3, a phased array imaging system 15 is connected to optical module 12 with nine laser diodes $S_1, S_2, \ldots, S_9$ and four PMTs $D_1, D_2, D_3, D_4$ (e.g., Hamamatsu R928, Hamamatsu R1645u, TO8) powered by a high voltage supply (not shown). Four laser diodes surround each PMT forming an equidistant arrangement (for example, different optical modules may use distances of 3.5, 7 and 10.5 cm). Switch 18 connects laser diodes $S_1, S_2, \ldots, S_9$ to a phase splitter 20, which provides to the diodes an RF modulation signal having both a 0 degree phase and a 180 degree phase. Imaging system 15 also includes a 50 MHz single side band transmitter 22 connected by a phase lock loop 24 to a 50 MHz single side band receiver 26. Single side band (SSB) transmitter 22 is connected to a 1 kHz oscillator 28, which provides a reference signal 30 to a phase detector 32. SSB receiver 26 is connected to a switch 27, which connects one of the four PMTs (0.5 µV sensitivity) depending on control signals from a controller 19. The SSB transmitter-receiver pair can operate in the frequency region of 10-1000 MHz (preferably 50-450 MHz). The phase noise of this apparatus is less than about 0.1°. The SSB receiver detects signal levels on the order of microvolts in a 2 KHz bandwidth. However, this narrow bandwidth limits the spread of switching of various light sources to approximately 1.0 msec, and thus the sequencing time for an entire image of 16 source detector combinations can be ~1 sec. The system uses a 1 sec averaging time.

Controller 19, connected to a personal computer (not shown), sequences laser diodes $S_1, S_2, \ldots, S_9$ so that two diodes receive 0° phase and 180° phase signals from splitter 20, every 0.1 sec. At the same time, controller 19 connects a symmetrically located PMT to SSB receiver 26. As shown in a timing diagram 40 (FIG. 3B), phased array imaging system 15 triggers two sources so that they emits modulated light of a 0° phase and a 180° phase for about 100 msec, and at the same time triggers a symmetrically located PMT. For example, when laser diodes 1 ($S_1$) and 2 ($S_2$) emit light of the 0° and 180° phase respectively, detector 1 ($D_1$) detects light that has migrated in the breast tissue. SSB receiver 26, which is phase locked with SSB transmitter 22, receives signal from detector 1 and provides output signal 34 to phase detector 32. Phase detector 32 measures the phase (36) of the detected light, and SSB receiver 26 provides the amplitude (38) of the detected light. This phase detection circuit was described in U.S. Pat. No. 4,972,331, which is incorporated by reference.

In the next cycle, controller 19 directs switch 18 to connect laser diodes 2 ($S_2$) and 3 ($S_3$), which emit modulated light of a 0° phase and a 180° phase, respectively, and detector 2 ($D_2$) detects light that has migrated in the breast tissue. Controller 19 also directs switch 27 to connect detector 2 to SSB receiver 26, which receives detection signal corresponding to the photons that have migrated from laser diodes 2 and 3 to detector 2. Again, phase detector 32 measures the phase (36) of the detected light, and SSB receiver 26 provides the amplitude (38) of the detected light. The duration of each pair of light flashes is 100 msec. The complete set of data for all source detector combinations is collected every 30 sec. A computer (not shown) stores the phase values and the amplitude values measured for the different combinations shown in timing diagram 40 and employs these values to create images of the examined tissue, as is described below. The computer uses the ADA2210 board for data acquisition.

Before or after the above-described measurement, phased array imaging system 15 may be calibrated on one or several models of the female breast. In the calibration procedure, the optical module is placed on the model and the imaging system collects the phase data and the amplitude data using the sequences shown in the timing diagram 40. The imaging system may use different breast models having the same scattering coefficient and the same absorption coefficient as the normal breast tissue of a female, for example, below 40 years and above 40 years. Due to the nature of the visible or infrared optical radiation, the described optical imaging systems may be used for breast tissue examination of a woman of any age. Furthermore, the models may have different sizes and have a shape of a female breast during examination. For example, the model has a shape of the breast (or the breast and a portion of the chest) of a woman lying on her back during examination.

Phased array imaging system 15 generates a "model" image for each wavelength employed. The model image may later be subtracted from the breast images to calibrate the system and also account for the boundary conditions of the light migrating in the tissue. Alternatively, phased array imaging system 15 is calibrated prior to taking measurement data and the gain on the light sources or the detectors is adjusted to obtain selected values.

Figure 3A:
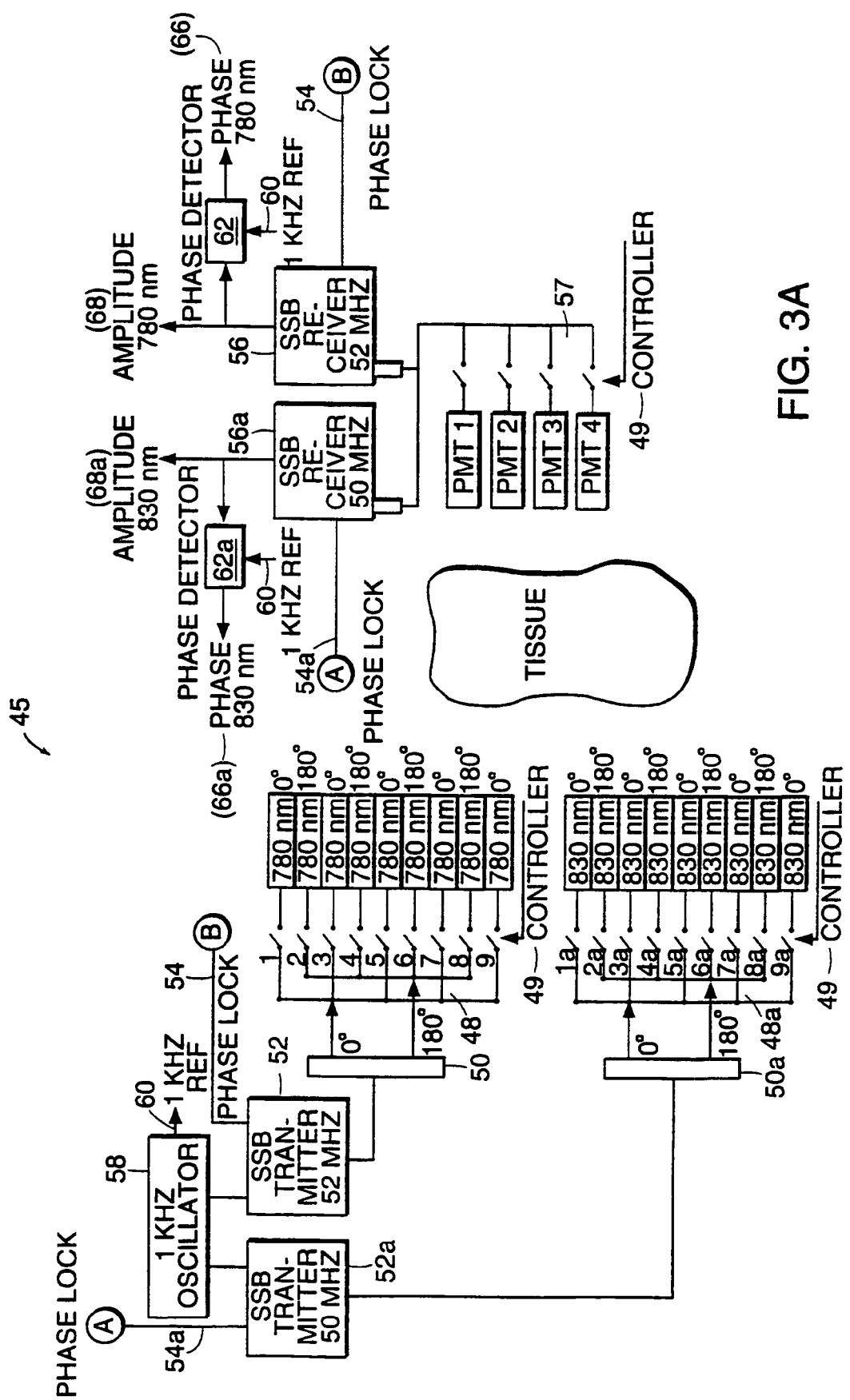

Referring to FIGS. 1A and 3A, a dual wavelength phased array imaging system 45 is connected to optical module 12 with nine 780 nm laser diodes $S_1, S_2, \ldots, S_9$, nine 830 nm laser diodes $S_{1a}, S_{2a}, \ldots, S_{9a}$, and the four PMTs $D_1, D_2, D_3$, and $D_4$ powered by a high voltage supply (not shown). Pairs of laser diodes $S_1$ and $S_{1a}$, $S_2$ and $S_{2a}, \ldots, S_9$ and $S_{9a}$ are located next to each other and arranged to introduce modulated light at almost the same tissue locations. A switch 48 connects laser diodes $S_1, S_2, \ldots, S_9$ to a phase splitter 50, which provides to the laser diodes an RF modulation signal having both a 0 degree phase and a 180 degree phase. Similarly, a switch 48a connects laser diodes $S_{1a}, S_{2a}, \ldots, S_{9a}$ to a phase splitter 50a, which provides to the laser diodes an RF modulation signal having both a 0 degree phase and a 180 degree phase. A 52 MHz SSB transmitter 52 is connected by a phase lock loop 54 to a 52 MHz SSB receiver 56, and a 50 MHz SSB transmitter 52a is connected by a phase lock loop 54a to a 50 MHz SSB receiver 56a. Both SSB transmitters 52 and 52a are connected to a 1 kHz oscillator 58, which provides a reference signal 60 to phase detectors 62 and 62a. SSB receivers 56 and 56a are connected to one of the four PMTs by a switch 57 depending on control signals from controller 49. Controller 49, connected to a personal computer, sequences the laser diodes so that two pairs of the laser diodes receive 0° phase and 180° phase signals from splitters 50 and 50a, and at the same time controller 49 connects a symmetrically located detector to SSB receivers 56 and 56a.

As shown in timing diagram 40 (FIG. 3B), phased array imaging system 45 triggers for each wavelength two sources that emit modulated light of a 0° phase and a 180° phase for about 100 msec and, at the same time, controller 49 connects the symmetrically located PMT. For example, switch 48 connects SSB transmitter 52 to 780 nm laser diode 4 ($S_4$) to emit 52 MHz modulated light of a 180° phase and connects 780 nm laser diode 5 ($S_5$) to emit 52 MHz modulated light of a 0° phase. At the same time, switch 48a connects SSB transmitter 52a to 830 nm laser diode 4a ($S_{4a}$) to emit 50 MHz modulated light of a 180° phase and connects 830 nm laser diode 5a ($S_{5a}$) to emit 52 MHz modulated light of a 0° phase. Simultaneously, switch 57 connects detector 1 ($D_1$) to SSB receivers 56 and 56a to receive the detection signal corresponding to photons of both wavelengths that have migrated in the breast tissue. Phase detector 62 provides the phase (66) of the detected 780 nm light, and phase detector 62a provides the phase (66a) of the detected 830 nm light for the selected geometry. Similarly, SSB receiver 56 measures the amplitude (68) of the detected 780 nm light and SSB receiver 56a measures the amplitude (68a) of the detected 830 nm light. This operation is repeated for all combinations of sources and detectors shown in timing diagram 40. A computer (not shown) stores the phase values and the amplitude values (at each wavelength) measured for the different combinations shown in timing diagram 40. The computer then uses the measured values to create images using algorithms included the enclosed source code.

Initially the system takes quick pictures to find the area of interest so that the optical module can be moved around to find an optimal geometry. Once found, the 780 nm and 830 nm data (i.e., both the phase and amplitude data) is acquired and saved on a disk.

Several phased array systems were described in the PCT application PCT/US 93/05868 (published as WO 93/2514 on Dec. 23, 1993), which is incorporated by reference. This PCT publication also describes the basic principles of phase and amplitude cancellation. The phased array imaging system uses a detector for detecting light emitted from equidistant sources located symmetrically with respect to the detector (or one source and several equidistant detectors located symmetrically). If two sources $S_1$ and $S_2$ emit modulated light having equal amplitude and a 0° phase and a 180° phase, detector $D_1$ located in the middle detects a null in the amplitude signal and detects a crossover between the 0° and 180° phase, i.e., a 90° phase, for substantially homogeneous tissue. That is, the detector is located on the null plane. In heterogeneous tissue, the null plane is displaced from the geometric midline. Nevertheless, the null establishes an extremely sensitive measure to perturbation by an absorber or scatterer. Furthermore, at the null condition, the system is relatively insensitive to amplitude fluctuations common to both light sources, and insensitive to inhomogeneities that affect a large tissue. The system has a high sensitivity to scattering provided that the scattering contrast is the same as the absorbing contrast. The system can readily observe shifts of 50 to 60° of phase under altered blood volume or blood oxygenation conditions, where the phase noise is less than a 0.1° (s/n>400) for a 1 Hz bandwidth. The amplitude signal is little less useful in imaging since the position indication is somewhat ambiguous, i.e., an increase of signal is observed regardless of the displacement of the absorbing object with respect to the null plane, although this is remedied by further encoding of the sources.

As described in the PCT application PCT/US 93/05868, the light sources excite a photon diffusion wave, which due to cancellation effects has a relatively long wavelength (~10 cm), determined by the scattering ($\mu_s'=10$ cm$^{-1}$) and absorption ($\mu_a=0.04$ cm$^{-1}$) properties of the tissue. The photon diffusion wavelength of about 10 cm provides imaging in the "near field." The imaging system may use light sources of one or several optical wavelengths in the visible to infrared range, depending on the characteristic to be imaged (i.e., blood volume, blood oxygenation, a distribution of a contrast agent in the tissue, an absorbing constituent of the tissue, a fluorescing constituent of the tissue, or other) The phase signal at zero crossing detection is essentially a square wave "overloaded" signal. It is moderately insensitive to the changes of signal amplitude that may occur in imaging from proximal to distal source-detector pairs and is also moderately insensitive to ambient light.

Figure 4:
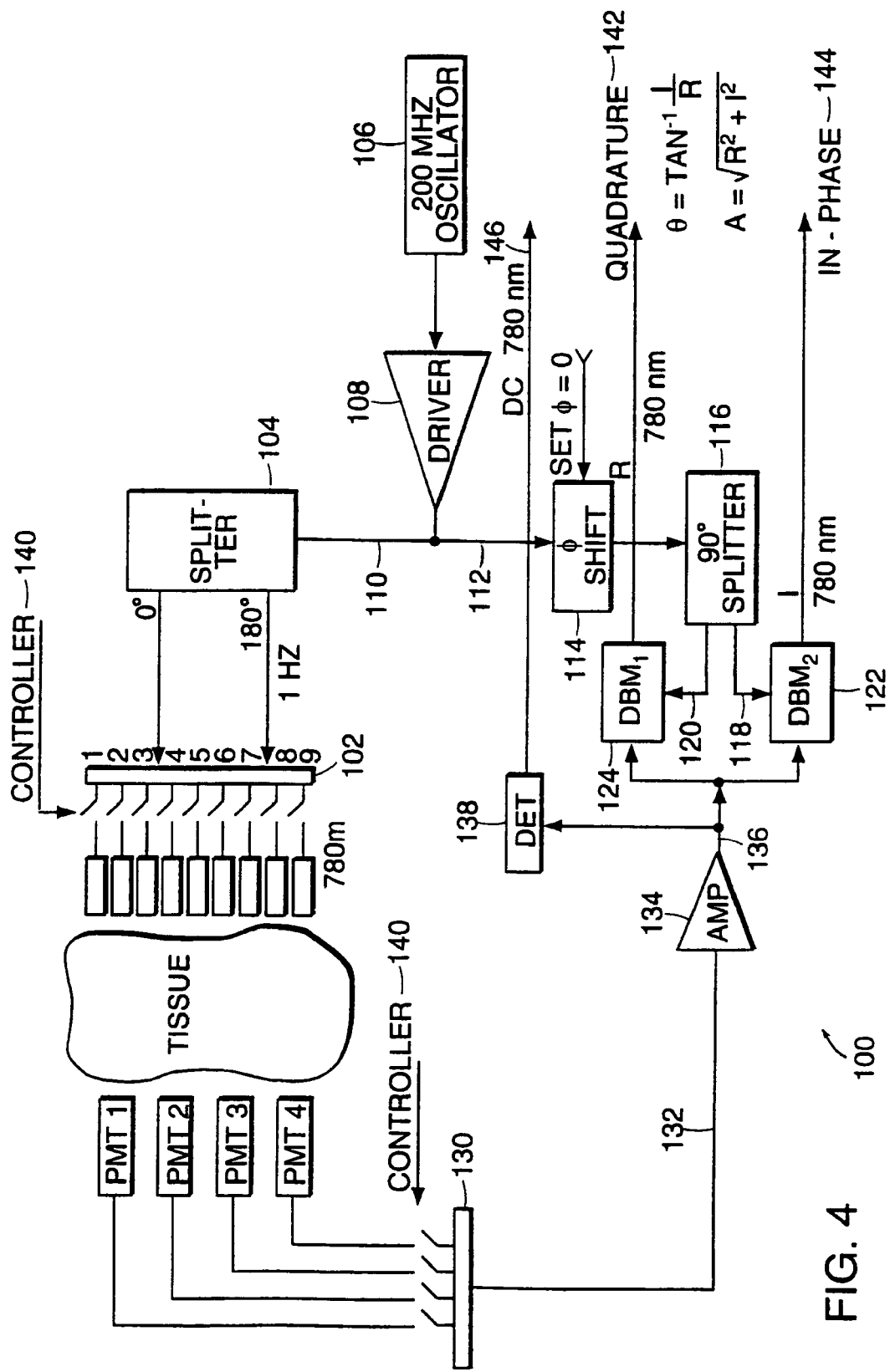
FIGS. 4 and 4A show diagrammatically another embodiment of the phase cancellation imaging system employing the optical module of FIG. 1A or FIG. 2A.

Referring to FIG. 4, in another embodiment, a phased array imaging system 100 is used instead of imaging systems 15 or 45. Imaging system 100, connected to optical module 12 (shown in FIG. 1A) having nine laser diodes $S_1, S_2, \ldots, S_9$ and four PMTs $D_1, D_2, D_3,$ and $D_4$, employs homodyne phase detection. A switch 102 connects laser diodes $S_1, S_2, \ldots, S_9$ to a phase splitter 104, which provides to the diodes an RF modulation signal having both a 0 degree phase and a 180 degree phase. Imaging system 100 also includes a 200 MHz oscillator 106 providing RF signal to a driver 108, which is connected to phase splitter 104. (Alternatively, an oscillator in the range of 10-1000 MHz, preferably 50-500 MHz, may be used.) A phase shifter 114 receives the drive signal (112) from driver 108 and provides the signal of a selected phase (e.g., a 0° phase change) to a 90° phase splitter 116. Phase splitter 116 provides a 0° phase signal (118) and a 90° phase signal (120) to double balance mixers (DBM) 122 and 124, respectively.

A controller 140, connected to a personal computer, sequences laser diodes $S_1, S_2, \ldots, S_9$ using switch 102 so that two diodes receive modulate signal at a 0° phase and a 180° phase signals from splitter 104. At the same time, a controller 140 connects a symmetrically located PMT using a switch 130 to an amplifier 134. Amplifier 134 provides a detection signal (136) to double balance mixers 122 and 124, and to a DC detector 138. Double balance mixer 122 receives the detection signal (136) and the 0° phase reference signal (118) and provides an in-phase signal I (144). Double balance mixer 124 receives the detection signal (136) and the 90° phase reference signal (120) and provides a quadrature signal R (142). DC detector 138 provides DC signal (146). The in-phase signal I and quadrature signal R specify the phase ($\theta=\tan^{-1}$ I/R) of the detected optical radiation and the amplitude ($A=(R^2+I^2)^{1/2}$) of the detected optical radiation. This phase detection circuit was described in U.S. Pat. No. 5,553,614, which is incorporated by reference.

Similarly as for imaging systems 15 and 45, imaging system 100 directs controller 140 to sequence the laser diodes and the PMT detectors using timing diagram 40. The computer stores the phase value and the amplitude value measured for each of the combinations and generates images described below.

Figure 4A:
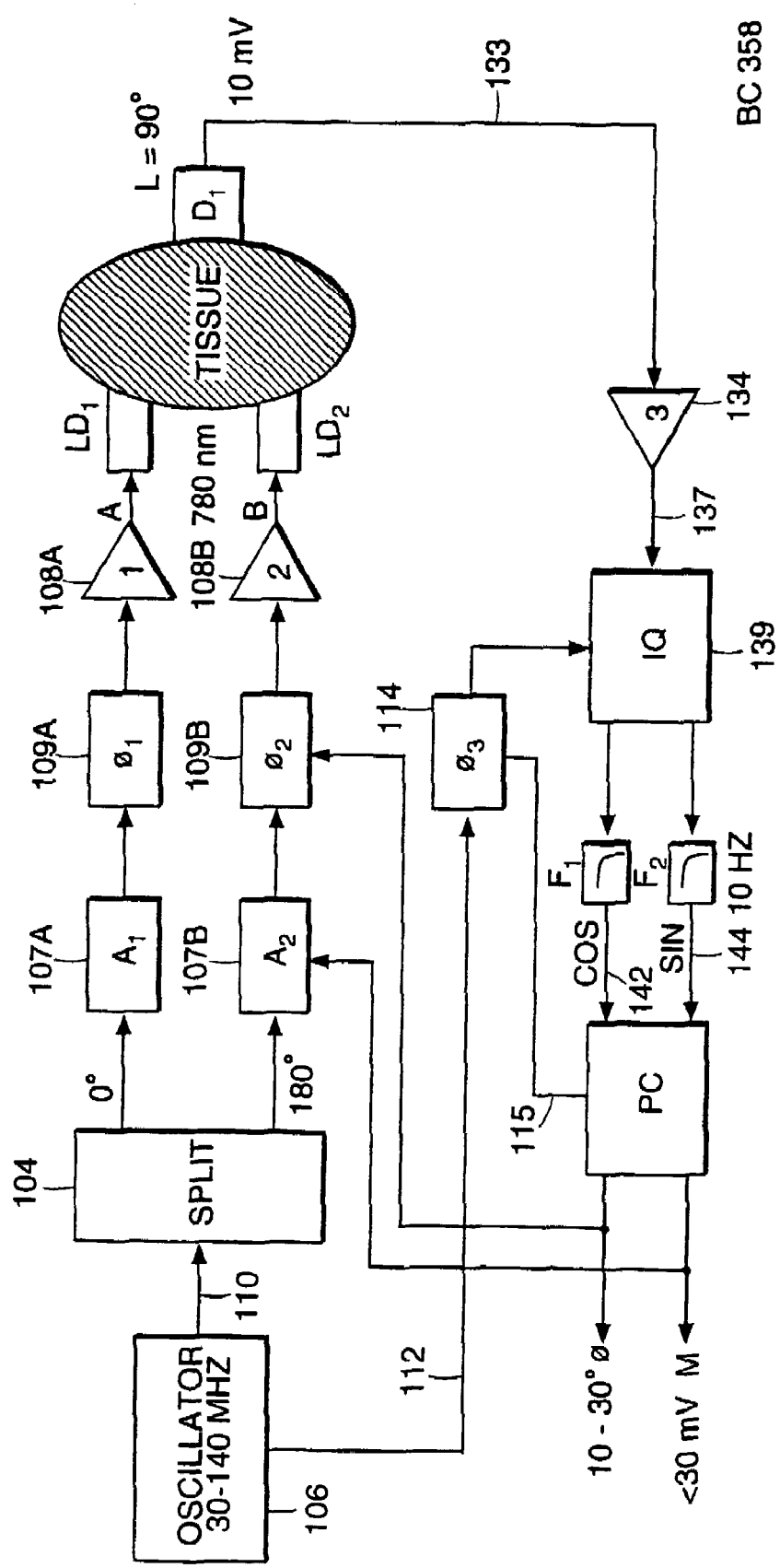

FIG. 4A shows diagrammatically one portion of phase cancellation, phased array imaging system 100. The depicted portion of imaging system 100 includes two laser diodes $LD_1$, and $LD_2$ and a light detector $D_1$, which are included in optical module 12 or 14. Oscillator 106 provides carrier waveform having a frequency in range of 30 to 140 MHz. The carrier waveform frequency is selected depending on the operation of the system. When time multiplexing the light sources using switch 102, then the carrier waveform is modulated at a lower frequency, e.g., 30 MHz to afford switching time.

When no time multiplexing is performed, oscillator 106 operates in the 100 MHz region. Splitter 104 splits the oscillator waveform into 0° and 180° signals that are then attenuated by digitally controlled attenuators 107A and 107B by 0% to 10% in amplitude. The phase of the attenuated signals is appropriately shifted by digitally controlled phase shifters 109A and 109B in the range of 10°-30°, and preferably 20° in phase. Laser drivers 108A and 108B drive $LD_1$ and $LD_2$, respectively, which emit light of the same wavelength, for example, 780 or 800 nm. After the introduced light migrates in the examined tissued, a PMT detector $D_1$ amplifies the detected signals having initially the 0 and 180° phases. As described above, for homogeneous tissue and symmetric locations of $LD_1$, $LD_2$ and $D_1$, the output of the PMT is 90°, i.e., halfway between 0° and 180° and the amplitude is close to zero. The personal computer (PC) adjusts the attenuation provided by attenuator 107B and the phase shift provided by phase shifter 109B so that detector $D_1$ detects phase nominally around 25° and amplitude nominally around $\leq 10$ millivolts for homogeneous tissue. This signal is connected to amplifier 134 and to the IQ circuit 139. The cosine and sine signals are fed into the personal computer, which takes the amplitude (the square root of the sum of the squares of I and Q) and the phase angle (the angle whose tangent is I/Q) to give outputs of phase around 25° and amplitude signals around 10 millivolts. The personal computer also adjusts the reference signal to the IQ to have the phase $\phi_3$ between 10° to 30° and preferably around 25°, i.e., phase shifter 114 provides to the IQ circuit 139 the reference phase having a value selected by the combination of phase shifters 109A and 109B.

In a currently preferred embodiment, splitter 104 is a two way 180° power splitter model number ZSCJ-21, available from Mini-Circuits (P.O. Box 350186, Brooklyn, N.Y. 11235-0003). The phase shifters 109A, 109B and 114 and attenuators 107A, and 107B are also available from Mini-Circuits, wherein the attenuators can be high isolation amplifier MAN-1AD. IQ demodulator 139 is a demodulator MIQY-140D also available from Mini-Circuits.

The system obtains the initial values of attenuator 107B ($A_2$) and phase shifter 109B ($\phi_2$) on a model or a symmetric tissue region (e.g., the contralateral breast that is tumor free). The entire probe is calibrated on a tissue model by storing the calibration values of $A_2$ and $\phi_2$ for the various source-detector combinations (i.e., the baseline image). The probe is then moved to the breast, for example, and the phases and amplitudes are detected for the various source and detector combinations. When the contralateral tumor free breast is used as a model, the probe is transferred to the contralateral breast (taking note to rotate the probe because of the mirror image nature of the breast physiology) and then the images are read out from all the source-detector combinations to acquire the tissue image. There is no limitation on multiplexing as long as the bandwidth of $F_1$ and $F_2$ is recognized as being the limiting condition in the system normalization. It should be noted that normalization must be accurate and without "dither" and therefore, a significant amount of filtering in $F_1$ and $F_2$, i.e., less than 10 Hz bandwidth. If $\phi_2$ is adjusted over a large range, there will be an amplitude-phase crosstalk. Thus, the system may adjust phase and then amplitude and repeat these adjustments iteratively because of the amplitude phase crosstalk. The control of $A_1$ and $\phi_1$ provides even a greater range of control, where obviously inverse signals would be applied to them, i.e., as the $A_1\phi_1$ signals are increased, the $A_2$, $\phi_2$ signals would be decreased. Both $A_2$ and $\phi_2$ can be controlled by PIN diodes, to achieve an extremely wideband frequency range. However, since signal processing controls the bandwidth of the feedback system, that either PIN diode or relay control of the phase and amplitude is feasible for automatic compensation. If, in addition, dual wavelength or triple wavelength sources are used, each one of them must be separately calibrated because no two light sources can be in the same position relative to the imaged tissue (unless, of course, they are combined with optical fibers).

Figure 5:
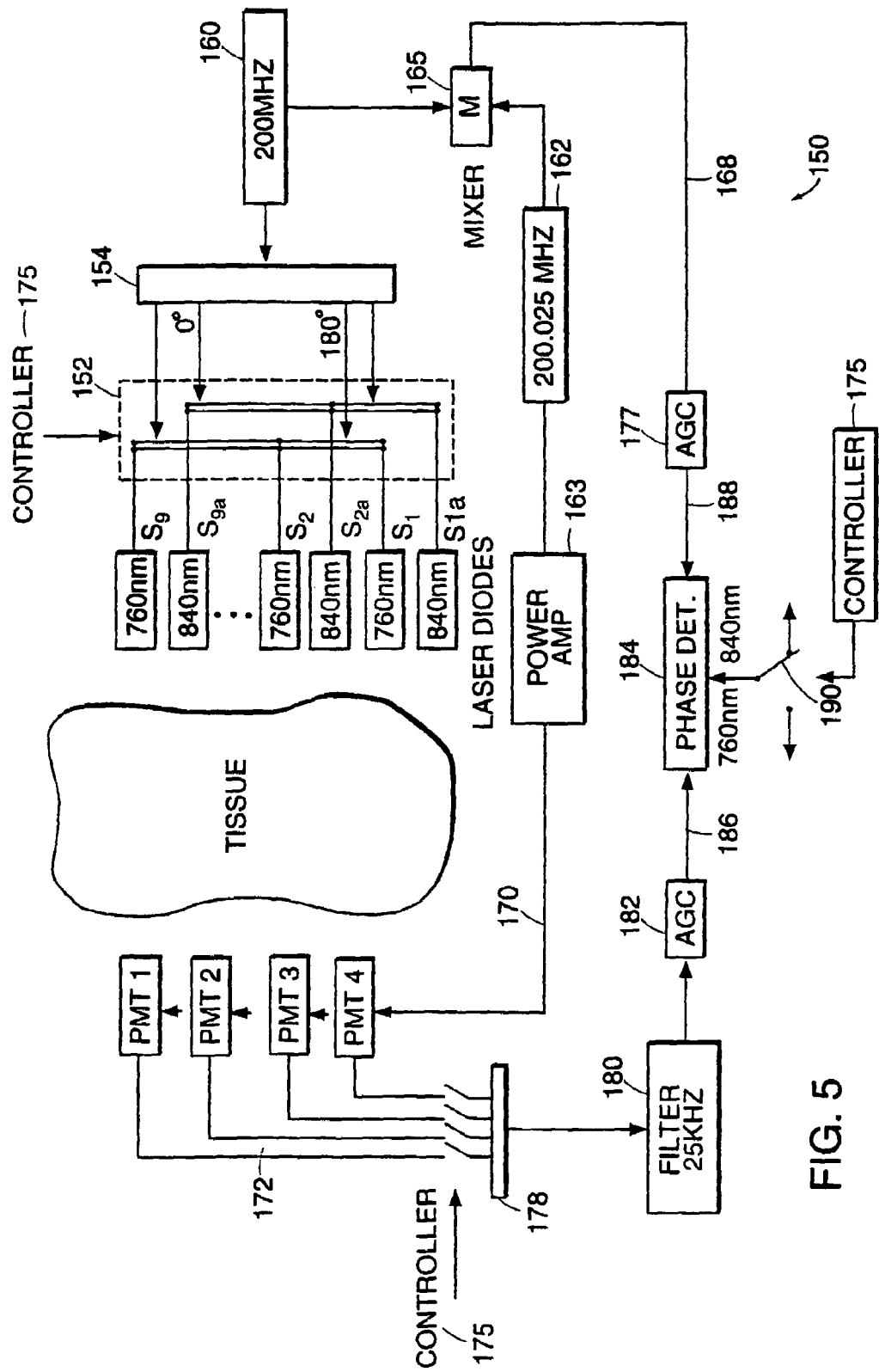
FIG. 5 shows diagrammatically another embodiment of the phase cancellation imaging system employing the optical module of FIG. 1A or FIG. 2A.

Referring to FIG. 5, in another embodiment, a dual wavelength phased array imaging system 150 is used instead of imaging systems 15, 45 or 100. Imaging system 150, connected to optical module 12 (shown in FIG. 1A) having nine 760 nm laser diodes $S_1$, $S_2$, . . . , $S_9$, nine 840 mm laser diodes $S_{1a}$, $S_{2a}$, . . . , $S_{9a}$ and four PMTs $D_1$, $D_2$, $D_3$, and $D_4$ is based on heterodyne phase detection. A switch 152 connects the laser diodes to a phase splitter 154, which provides to the diodes an RF modulation signal having both a 0 degree phase and a 180 degree phase. Imaging system 150 employs a mixer 165 connected to a 200 MHz oscillator 160 and 200.025 MHz oscillator 162 (Alternatively, oscillators operating in the range of 10-1000 MHz, preferably 50-500 MHz, may be used.) Mixer 165 provides a 25 kHz reference signal (168) to an adjustable gain controller 177. Oscillator 162 connected to power amplifier 163 provides a 200.025 MHz reference signal (170) to the second dynode of each PMT detector for heterodyne detection. Each PMT detector provides a 25 kHz detection signal (172) to a switch 178, which in turn provides the signal to a 25 kHz filter 180. A phase detector 184 is connected to an adjustable gain controller 182, which provides a filtered and amplified detection signal (186) and to adjustable gain controller 177, which provides the reference signal (188). Phase detector 184, connected to a switch 190, provides the detected phase value for each wavelength. This phase detection circuit was described in U.S. Pat. No. 5,187,672, which is incorporated by reference. Another type of phase detection circuit was described in U.S. Pat. No. 5,564,417, which is incorporated by reference.

Similarly as described above, controller 175, connected to a personal computer, sequences laser diodes $S_1$, $S_2$, . . . , $S_9$ or laser diodes $S_{1a}$, $S_{2a}$, . . . , $S_{9a}$ using switch 152 so that two diodes emitting the same wavelength receive 0° phase and 180° phase signals from splitter 154. At the same time, controller 175 connects a symmetrically located PMT using a switch 178 to filter 180 and adjustable gain controller 182. Phase detector 184 provides the measured phase. Imaging system employs timing diagram 40 (FIG. 3B); however, since the two wavelength light is not frequency encoded, laser diodes $S_1$, $S_2$, . . . , $S_9$ or laser diodes $S_{1a}$, $S_{2a}$, . . . , $S_{9a}$ are triggered in each sequence. The computer stores the phase values measured for the different combinations and generates images described below.

Figure 6:
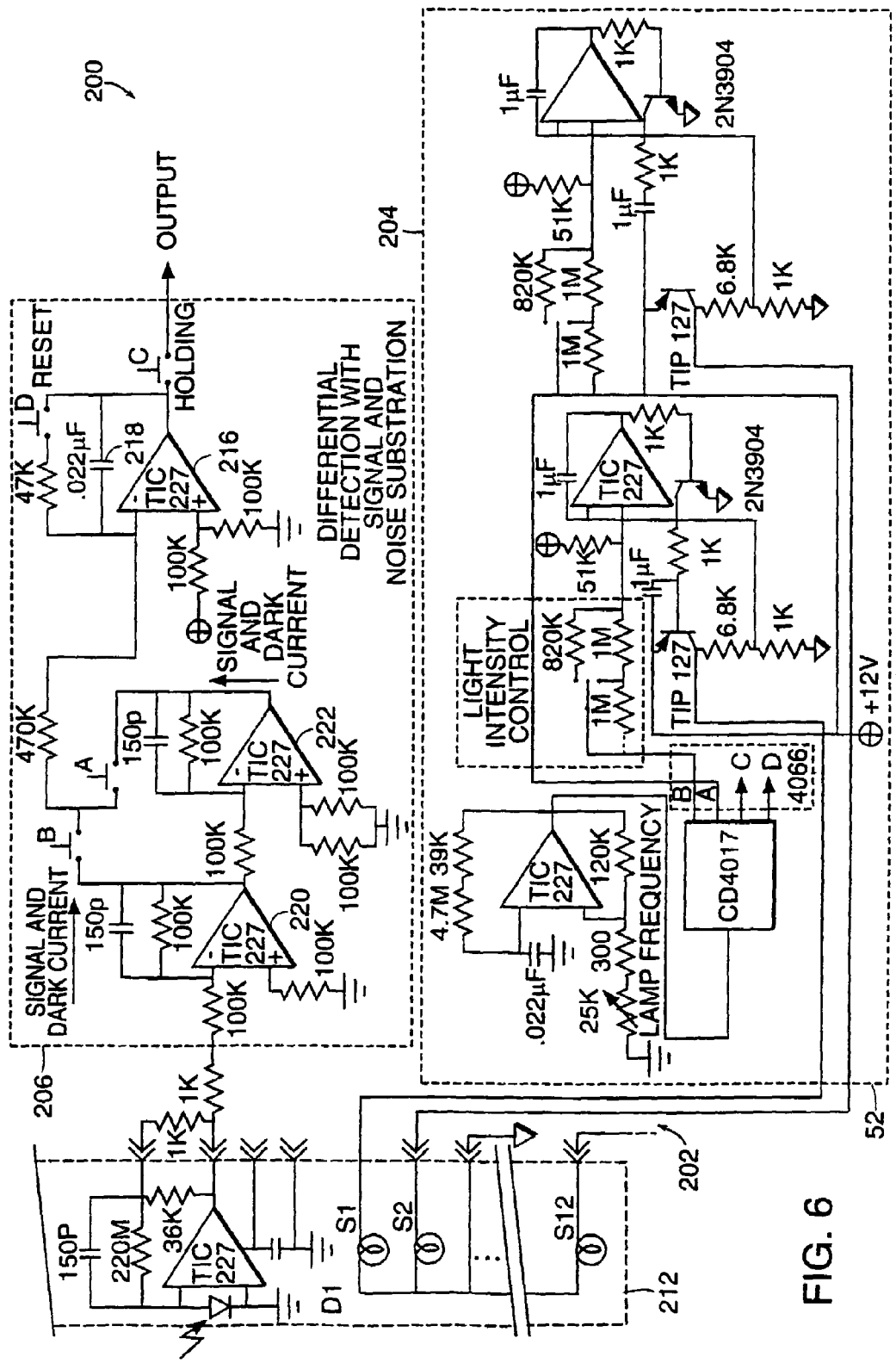
FIG. 6 shows schematically an amplitude cancellation imaging system using another embodiment of the optical module shown in FIG. 6A.
Figure 6A:
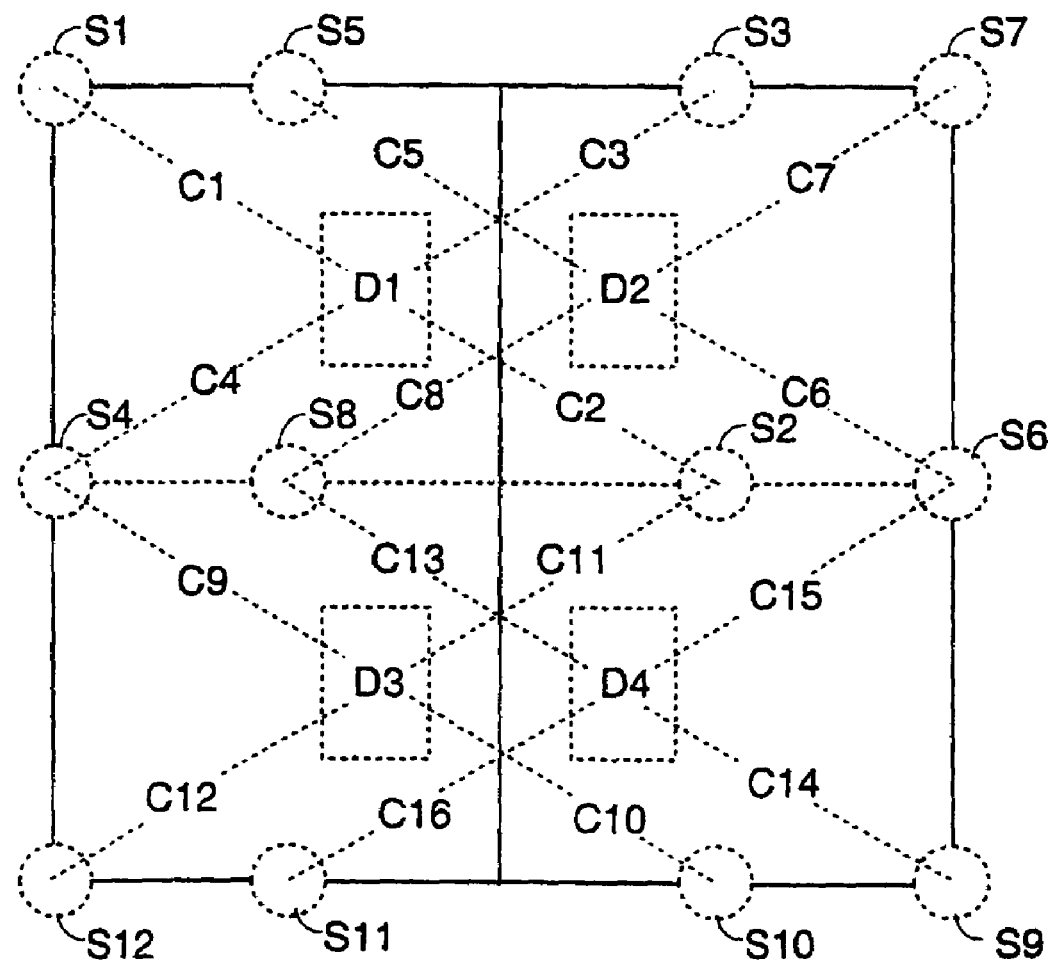

Referring to FIG. 6, in another embodiment, an amplitude cancellation imaging system 200 uses an optical module 212 shown in FIG. 6B. Optical module 212 includes twelve light sources S1, S2, . . . , S12 and four light detectors D1, D2, D3, and D4 mounted on a plastic or rubber foam material. The light sources and the light detectors are located on a geometrical pattern that provides sixteen source-detector combinations (C1, C2, ..., C16) having a selected source-detector separation. The separation may be 2.5 cm to produce about 1.25 cm average light penetration. (Several modules with different source-detector separations may be used to obtain several two dimensional images of different tissue depths. Alternatively, a single module may include source detector combinations providing different separations.) The light sources are 1 W tungsten light bulbs, which emit broad band non-modulated light. The light detectors are silicon diodes, each equipped with an interference filter transmitting a 10 nm wide band centered at 760 nm and 850 nm. The 760 nm and 850 nm wavelengths are selected to detect oxyhemoglobin and deoxyhemoglobin in the examined tissue.

Optical module 212 is connected to an analog circuit 202, which includes a source circuit 204 for controlling sources S1, S2, ... S12. Optical module 212 is connected to a detector circuit 206, which controls diode detectors D1, D2, D3 and D4. In general, imaging system 200 can turn ON each source for a selected period in the range of $10^{-6}$ sec. to 0.1 sec., and one or several symmetrically located detectors are turned on simultaneously or sequentially to collect optical data. Specifically, as provided in Appendix B, one of sources S1, S2, ... S12 is turned ON for 500 msec and the emitted light is introduced into the tissue from the corresponding input port. The introduced photons migrate over banana shaped paths in the examined tissue to a detection port. The corresponding detector is triggered 200 msec. after the source and collects light for 200 msec. A detection circuit 206 receives a detector signal from the diode detector. Detection circuit 206 enables correction for the dark current/noise that comprises background light, DC offset of the operational amplifiers, photodiode dark current, temperature effects on the outputs of individual components and variations due to changing environment.

Imaging system 200 performs data acquisition in four steps synchronized by its internal oscillator. The first step is performed by having the light sources OFF. The detector output is directed to an integrator 216 and integration capacitor 218 is charged to the dark level voltage. In the second step, the light source is turned ON and after 200 msec the preamplifier output that corresponds to the intensity of the detected light is directed to integrator 216 in a way to charge capacitor 218 with current of polarity opposite to the polarity of the charging current in the first step. This is achieved using an appropriate ON/OFF combination of switches A and B. The voltage of capacitor 218 is charging to a value that, after 200 msec., represents the total detected intensity minus the dark level noise signal. In the third step, both switches A and B are turned OFF to disconnect both the positive unity gain and the negative unity gain operational amplifiers (220 and 222). Then, the output of integrator 218 is moved via switch C to an analog-to-digital converter and the digital signal is stored in the memory of a computer. In the fourth step, the switches A, B and C are open and switch D is closed in order to discharge capacitor 218 through a 47K resistor. At this point, the circuit of integrator 216 is reset to zero and ready for the first step of the detection cycle.

Alternatively, analog circuit 202 may be replaced by a computer with an analog-to-digital converter and appropriate software that controls the entire operation of optical module 212. An algorithm that controls the sources and the detectors of optical module 212 in a similar way as described above. The detected dark level noise signal is digitally subtracted from the detected intensity of the introduced light.

The collected data sets are processed using an imaging algorithm. The imaging algorithm calculates the blood volume of the examined tissue for each source-detector combination for each data set. The imaging algorithm can also calculate the oxygenation of the examined tissue for each source-detector combination.

The blood volume or oxygenation images can be subtracted from "model" images. The blood volume image can be subtracted from the oxygenation image to create congruence data to localize and characterize a tissue anomaly. That is, the imaging algorithm creates an image using the differential image data sets. Prior to creating the image, an interpolation algorithm is employed to expand the differential image data set, containing 16 (4×4) data points, to an imaging data set containing 32×32 image points.

Alternatively, the computer uses a back-projection algorithm known in computed tomography (CT), which is modified for light diffusion and refraction and the banana like geometry employed by the optical imaging system. In the optical back-projection algorithm, the probabilistic concept of the "photon migration density" replaces the linear relationship of ballistically transmitted X-rays, for the beam representing pixels. The photon migration density denotes a probability that a photon introduced at the input port will occupy a specific pixel and reach the detection port. For different types of tissue, the phase modulation spectrophotometer provides the values of the scattering and absorption coefficients employed in the probability calculations. In the image reconstruction program, the probability is translated into a weight factor, when it is used to process back-projection. Back-projection algorithms known in CT may be used. The back-projection averages out the values of information that each beam carries with the weighting in each pixel. A weighting algorithm for creating a photon density image may be used in the back-projection reconstruction algorithm described above.

A method for correcting blurring and refraction used in the back-projection algorithm was described by S. B. Colak, H. Schomberg, G. W.'t Hooft, M. B. van der Mark on Mar. 12, 1996, in "Optical Back-projection Tomography in Heterogeneous Diffusive Media" which is incorporated by reference as if fully set forth herein. The references cited in this publication provide further information about the optical back-projection tomography and are incorporated by reference as if fully set forth herein.

Another embodiment of the amplitude cancellation imaging system 200 uses optical module 14 shown in FIG. 2A. In this arrangement, four centrally located light sources S1, S2, S3, and S4 and 21 detectors D1, D2, ..., D21 provide a multiplicity of symmetric photon migration paths for each source. For example, source S1 is turned ON for a period in the range of $10^{-6}$ sec. to 0.1 sec. The source emits non-modulated light into the breast tissue. Symmetrically located detectors D1 and D11 are ON simultaneously to collect introduced photons migrating over substantially symmetric paths. For normal breast tissue, detectors D1 and D11 detect light of the same intensity, and thus the differential signal is zero, i.e., the detected amplitude are canceled. Imaging system 200 collects the differential data for a multiplicity of symmetric photon migration paths and generates an image of the examined tissue. Imaging system 200 may collect optical data for several wavelengths and generate blood volume images and blood oxygenation images for the examined tissue. Amplitude cancellation imaging system 200 may also use a second identical optical module 14 placed on the opposite breast. The blood volume or oxygenation images collected for the two breasts may be subtracted to provide a differential image, which will further emphasize a tissue abnormality located in one breast.

Alternatively, the amplitude cancellation imaging system uses light modulated at frequencies in the range of 0.1 to 100 kHz. The system employs the above-described algorithm, but the light sources emit frequency modulated light and the detectors, each connected to a lock-in amplifier, detect light modulated at the same frequency. This lock-in detection may further increase the signal to noise ratio by eliminating external noise. The detected light intensities are processed the same way as described above to image the examined tissue.

Figure 7:
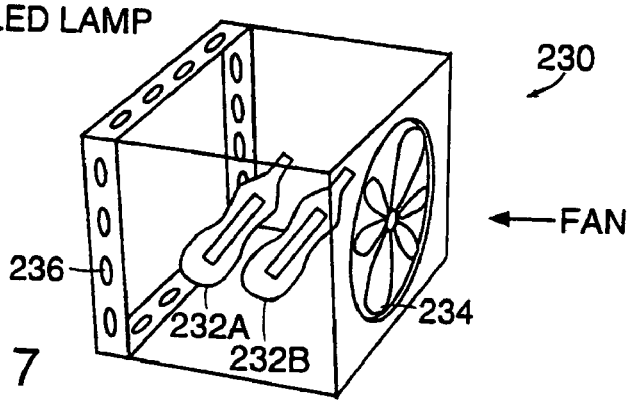
FIGS. 7, 7A and 7B show different embodiments of a cooling module used with a broad band light source, such as a tungsten light bulb.
Figure 7A:
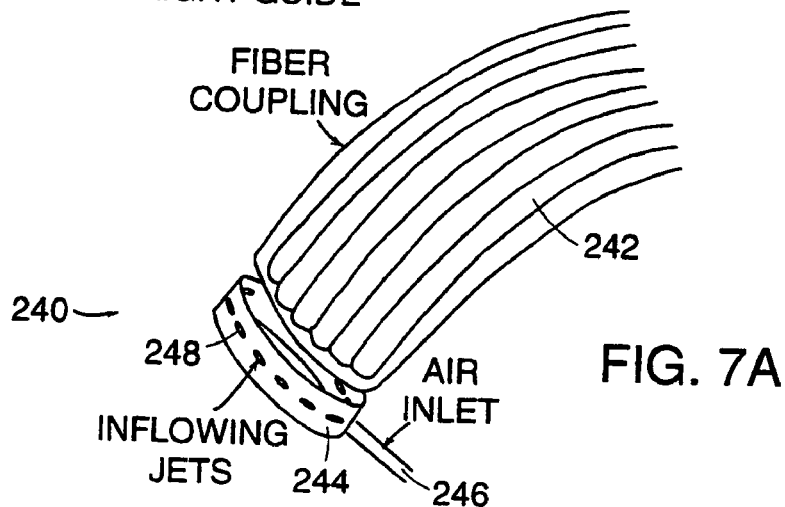
Figure 7B:
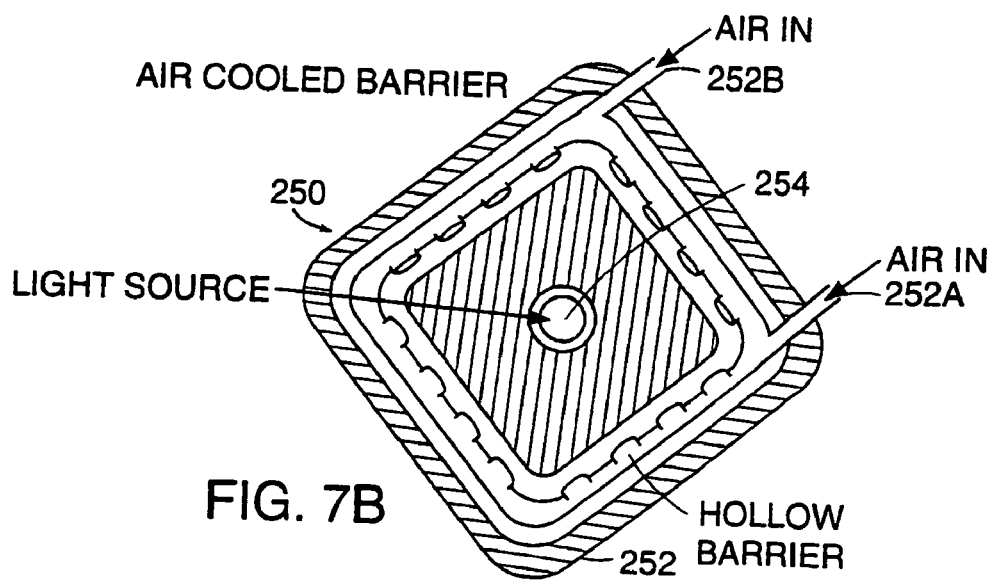

FIGS. 7, 7A and 7B show different embodiments of a cooling module used with a broad band light source or light guides, where they are positioned close to the skin. In this arrangement, there is trapped heat that frequently causes an uncomfortable temperature. FIG. 7 depicts a cooling module 230, which surrounds light sources 232A and 232B. Cooling module 230 includes a fan 234 and a set of air passages 236. In a similar design, two fans are juxtaposed on each side of one or more light bulbs to form an "open frame" so that the fans blow not only upon the light sources, but upon the skin itself. The cooling module enables a power increase on the light sources, but no increase of heat upon the skin itself, which remains under comfortable conditions.

FIG. 7A depicts a cooling module 240 for cooling light guides. Light guides 242 deliver light and heat to the skin. A cooling ring 244 includes an air inlet 246 and a set of air passages 248 (or jets) for providing air flow to the irradiation location. FIG. 7B depicts a cooling module 250 constructed to air cool a light barrier 252. Light barrier 252 has similar optical properties as the light barrier described in the PCT application PCT/US92/04153 (published on Nov. 26, 1992 as WO 92/20273), which is incorporated by reference. This embodiment utilizes the advantages of the light barrier and enables the use of higher light intensities. Cooling module 250 includes air inlets 252A and 252B, which provide air to a set of conduits and openings that deliver air to the skin near light source 254. Compressed air may also be used.

The intensity regulations for delivering continuous otherwise noncoherent light to the skin often depend on the temperature rise of the skin itself. For examination of large tissue volumes or deep tissues (i.e., where there is a large separation between the optical input and optical detection ports) relatively large light intensities are needed. Under conditions of prolonged even low level illumination, the skin may become uncomfortably warm and may blister. However, the erythemic effects are much smaller in the NIR, where the delivered heat is a factor, than they are in UVA and UVB, where cancer-producing damage may occur (but is not known for the NIR). The effect of the cooling air is not just convection of warm air away from the skin, but it enhances the evaporation of perspiration from the skin. Thus, as soon as the skin temperature rises and perspiration is initiated, greatly enhanced cooling is obtained with the forced air increasing the evaporation.

Figure 8:
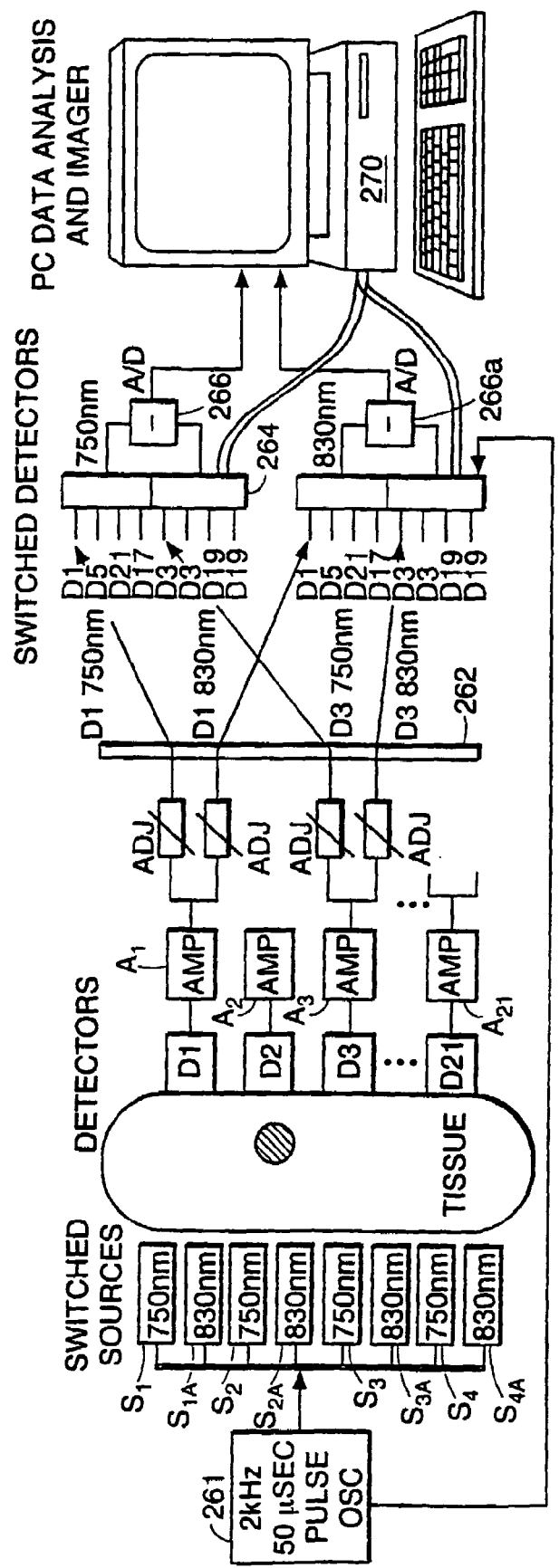
FIG. 8 shows diagrammatically another embodiment of the amplitude cancellation imaging system employing the optical module of FIG. 2A.

Referring to FIG. 8, an amplitude cancellation imaging system 260 is used instead of imaging systems 15, 45, 100, 150, or 202. Dual wavelength amplitude cancellation imaging system 260 is connected to optical module 14 shown in FIG. 2A and includes four 750 nm laser diodes $S_1$, $S_2$, $S_3$, and $S_4$, four 830 nm laser diodes $S_{1a}$, $S_{2a}$, $S_{3a}$, and $S_{4a}$, and twenty-one silicon diode detectors $D_1$, $D_2$, ..., $D_{21}$. Each detector is connected to a preamplifier and an adjustable gain controller that may be used initially for calibration. The detector outputs are switched by a switch 262 by a controller 264 so that analog-to-digital converters 266 and 266a receive 750 nm and 830 nm data, respectively, from two symmetrically located detectors. A computer 270 stores the detected values measured for the different combinations using algorithms employed in the enclosed source code. The computer also generates images described below. Another type of amplitude detection circuit was described in FIGS. 11 through 13 and the corresponding specification of U.S. Pat. No. 5,673,701, which is incorporated by reference as if fully set forth herein.

Figure 8A:
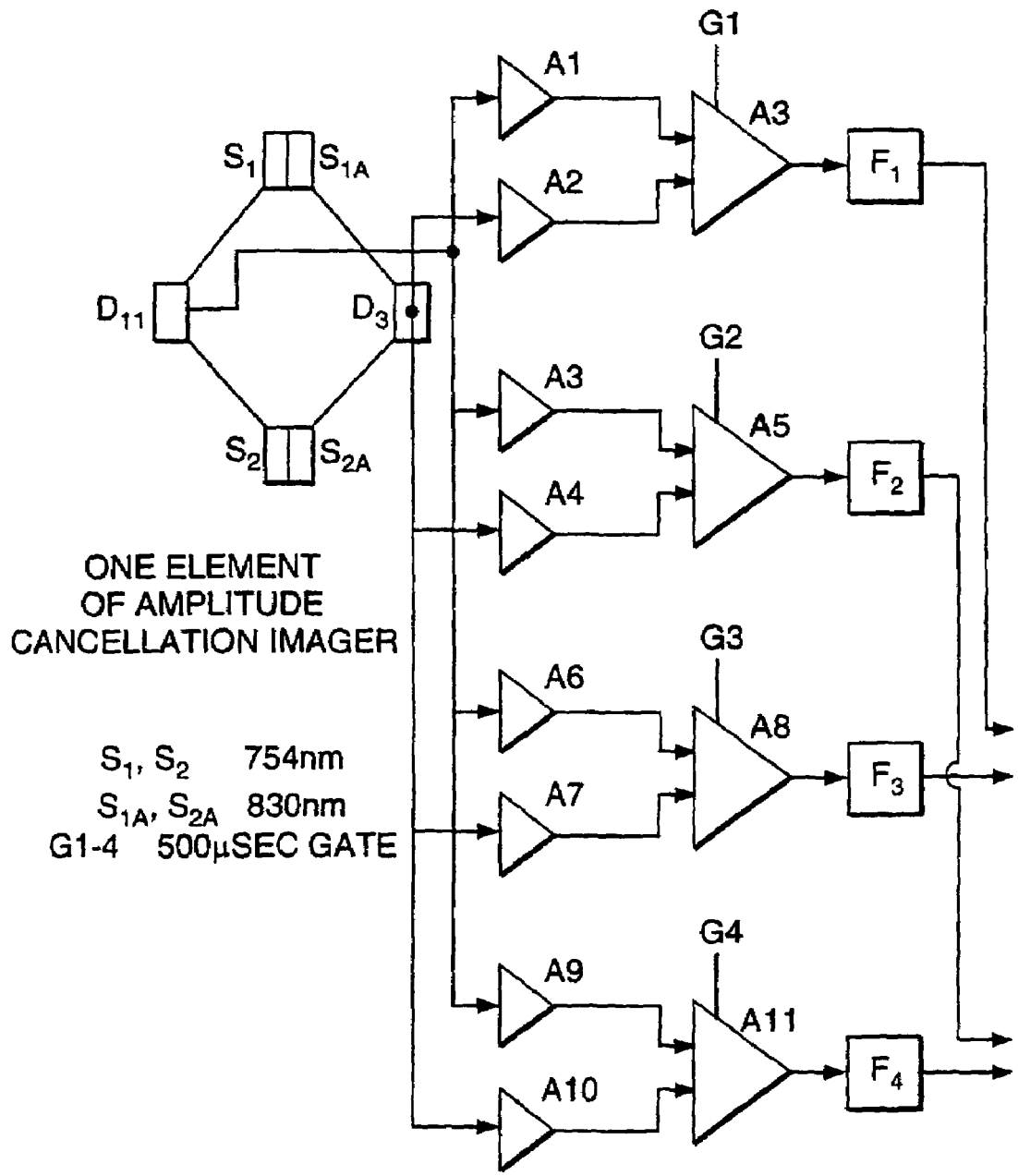
FIG. 8A shows a circuit configuration for one element of the amplitude cancellation imaging system of FIG. 8.
Figure 8B:
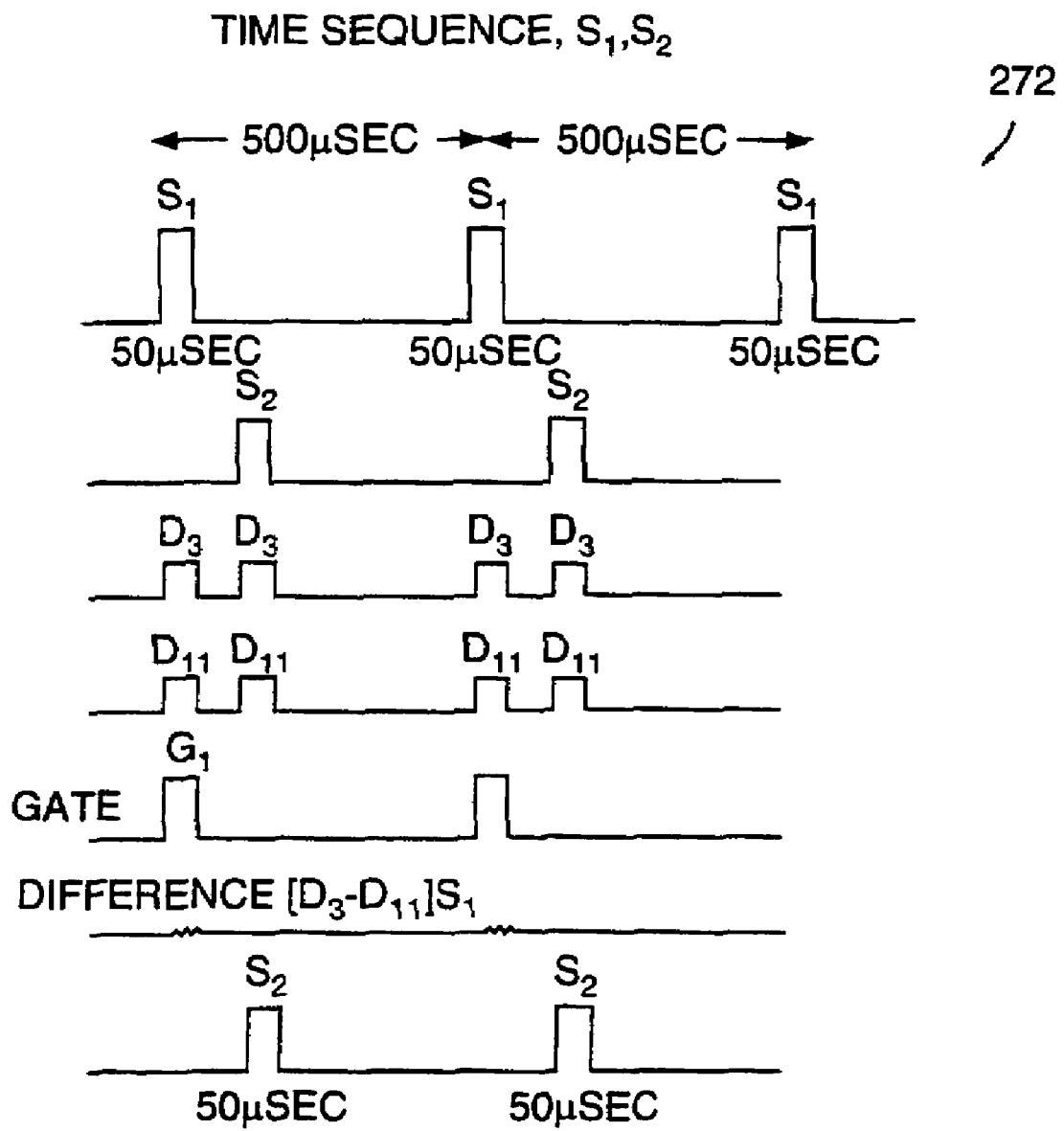
FIG. 8B is a timing diagram used by the imaging system of FIG. 8.

Also referring to FIGS. 8A and 8B, the controller sequences an oscillator 261 so that each source emits a 50 μsec light pulse as shown in timing diagram 272. The system sequences through the various source/detector combinations in approximately one msec, and averages the imaged data over 8 sec to get a very high signal to noise ratio. The circuit configuration for one element of imaging system 260, i.e., 754 nm sources $S_1$, $S_2$ and 830 nm sources $S_{1a}$, $S_{2a}$, and two symmetrically positioned detectors $D_3$ and $D_{11}$, is shown in FIG. 8A. The light intensities detected for the symmetrical locations are subtracted in a digital or analog way. The computer stores all data detected for the two wavelengths for generating tissue images.

Figure 8C:
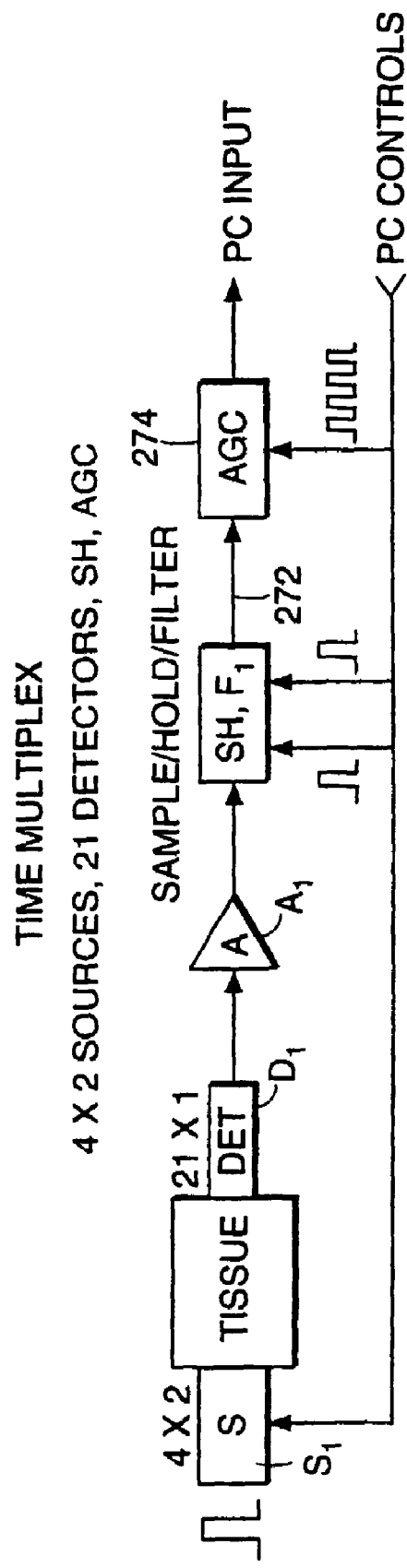
FIG. 8C shows diagrammatically one channel of the amplitude cancellation imaging system of FIG. 8.

FIG. 8C shows diagramatically a single channel 260A of the time multiplex imaging system 260. Detector $D_1$ detects light emitted from light source $S_1$ emitting light pulses of the duration of about 50 μsec. The detector signal is amplified and provided to a sample-and-hold circuit and filter. Detector $D_1$ is a silicon diode detector that has the detection area of about 4×4 mm and includes a pre-amplifier. The filtered signal 272 is provided to an AGC 274, which adjusts the amplitude of the signal based on a control signal from a personal computer. The personal computer has normalization amplitudes for the individual source-detector combinations.

Amplitude cancellation imaging system 260 is normalized on a tissue model by detecting signals for the individual source-detector combinations and appropriately normalizing the detected signal using the AGC control. The individual normalization/calibration amplitudes form a baseline image that is stored in the computer. As described above, the baseline image may also be acquired on a symmetric tissue region, such as the contralateral breast for breast tissue examination or the contralateral brain hemisphere for brain tissue examination. The normalization process can be repeated several times to account for drifts in the individual elements. During the measurement process, the personal computer can adjust the gain of each AGC 314 based on the calibration values that account only for the electronic drift. Then, the defected image is subtracted from the baseline image of the examined tissue. Alternatively, while collecting the measurement data on the examined tissue, the measurement image is subtracted from the baseline image to create the tissue image that includes any tissue in homogeneities such as a tumor or bleeding. The sample-and-hold circuit may be an analog circuit or the sample-and-hold function, including the filtering, may be performed digitally.

Figure 8D:
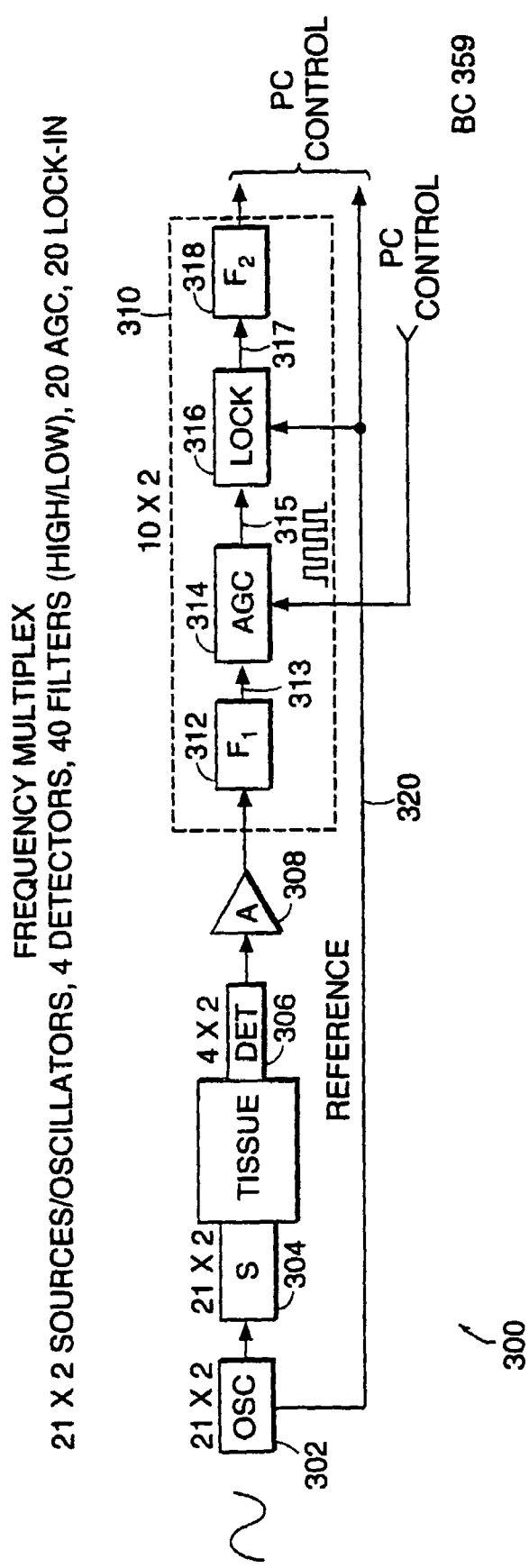
FIG. 8D shows diagrammatically another embodiment of the amplitude cancellation imaging system of FIG. 8.

FIG. 8D shows diagramatically an amplitude cancellation imaging system employing a frequency multiplex method. Amplitude cancellation system 300 includes 21 oscillators 302 operating a frequencies in the range of 1 kHz to 100 kHz. Each oscillator 302 drives a light source 304 (for example, a laser diode or LED), which emits an intensity modulated light into the examined tissue. Each light detector 306 (for example, a photomultiplier, an avalanche photodiode PIN detector or a silicon detector) detects the intensity modulated light and provides a detector signal to an amplifier 308. The amplified detector signal is provided to a processing channel 310, which includes a band pass filter 312, an AGC 314, a lock-in amplifier 316, and a filter 318. Filter 312 filters the detector signal, and AGC 314 adjusts the amplitude according to the input signal from a personal computer. Lock-in amplifier 316 receives the amplified signal 315 and a reference signal 320 from oscillator 302. Lock-in amplifier 312 provides amplitude signal 317 to filter 318. Processing channel 310 may be an analog channel or a digital channel.

In the amplitude cancellation system 310, all light sources emit light at the same time into a selected tissue region. Each light source is modulated at a distinct frequency in the range of 1 kHz to 100 kHz. In order to resolve the modulated light signals and attribute them to the individual light sources, the oscillators operate at frequencies 1 kHz, 2 kHz, 4 kHz, 8 kHz, 16 kHz, . . . Filters 312 and 318 are designed to provide only the detection signal from a selected light source, and lock-in amplifier 312 provides the amplitude of the signal at the selected frequency. Frequency multiplex system 300 is calibrated the same way as the time multiplex system 260, and the normalization/calibration amplitude values are also stored in the personal computer. The images are processed as described above.

All above-described imagers will achieve a higher spacial resolution of the imaged tissue by increasing the number of sources and detectors. Furthermore, the sources and detectors may form various 1 dimensional, 1.5 dimensional, or 2 dimensional arrays as described in the above-referenced documents.

Figure 1C:
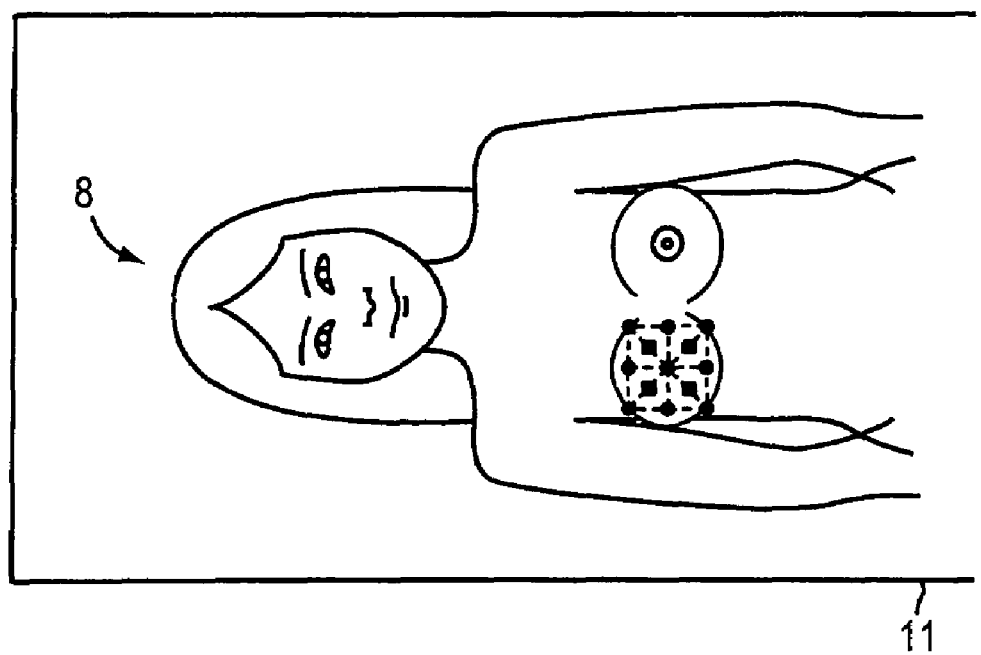

In a clinical study, which is provided only as an illustrative example, a number of female patients were examined using three different positions. First, the patients were sitting upright supporting the breast by the imager optical module. Second, the patients were lying face down with the breast on the optical module pad, and third, the patients were lying supine, on examination table 11, face up with the breast spread over the chest as evenly as possible as shown in FIGS. 1B and 1C. In the third position, the patients were lying on their back. This position with the flattened adipose breast is the optimal position for imaging of a suspicious mass in patients over 40 years old. The third position is also preferred for patients below 40 years since the matching tissue background of the chest muscles and the ribcage provides suitable boundary conditions. In this position, no matching fluid was used. The thickness of the examined tissue with this geometry is usually no more than 4 to 5 cm even for a large breast.

Initially, the imager was first calibrated on a breast model. During the examination, the patient or the attendant held optical probe 14 over a designated portion of the breast. The mirror image region on the contralateral breast was also recorded. The images were acquired in 8 sec from each breast taking advantage of a priori information obtained by palpation, X-ray mammography, ultrasound examination, fMRI, or a needle biopsy. Other images were taken having only palpation information so that the 10×10 $cm^2$ active area of optical probe 14 covered the suspicious mass. The positioned probe may or may have not included the nipple, which is clearly visible on the optical images.

The optical images were created using a back-projection algorithm. The images may be displayed in the format of the left breast data minus the model data, the right breast data minus the model data for each wavelength (e.g., 750 and 830 nm). Alternatively, the model calibration may be performed by adjusting the detector gains prior to the breast measurements. Furthermore, the images may be the differential between the right breast and the left breast for each wavelength to emphasize any tissue difference, such as a suspicious mass, which is unlikely located symmetrically in both breasts. The images may also be processed to image blood volume and blood oxygenation of the examined tissue of each breast. The blood volume image is the sum of 0.3 times the 750 nm data and 1.0 times the 830 nm data. The blood deoxygenation image is the difference of the 750 nm and the 830 nm data. The above coefficients were derived from blood tests in model systems. The images have the highest specificity and sensitivity when the contralateral breast data is used as a baseline and both the blood volume data and the hemoglobin deoxygenation data is imaged and positional compared.

The blood volume and hemoglobin deoxygenation images provide an important tool in characterizing a suspicious anomaly in the examined breast. While the blood volume, hemoglobin oxygenation images and hemoglobin deoxygenation images, as well as the single wavelength images, are useful in locating an abnormal tissue region (i.e., detecting the abnormal structure), these images are also used to characterize the metabolism or pathology of the suspicious tissue anomaly. Specifically, an increased blood volume signal is observed with respect to the adipose tissue background due to the increased vascularity of a tumor as a consequence of angiogenetic factors. These factors include actively metabolizing regions and necrotic/apoptotic regions of the tumor. On the other hand, the hemoglobin deoxygenation signal is related to metabolic intensity. That is, the balance between oxygen delivery and oxygen uptake, which in tumors is usually balanced in favor of oxygen uptake exceeding oxygen delivery. The increased oxygen uptake occurs particularly for those tumors that are aggressively growing, and may well be metastatic.

By selecting an appropriate wavelength, or several wavelengths, sensitive to an optically active tissue property, the imaging system can non-invasively characterize a tissue anomaly. The above-mentioned wavelengths are sensitive to hemoglobin and hemoglobin oxygenation, but other wavelengths sensitive to absorption by any tissue constituent may be used. Furthermore, an optical contrast agent (e.g., cardiogreen, indocyanine green) may be injected intravenously. The imaging system will then use a wavelength sensitive to the administered contrast agent. The regions of increased blood volume will also have a higher content of the contrast agent.

Alternatively, differences in tissue scattering may be imaged. Due to differences in the optical refractive index, different types of tissue and different tissue solutes scatter light differently. The above-described imaging systems are also sensitive to scattering changes. The imaging system may use a wavelength that does not exhibit absorption changes for different types of tissue and different tissue solutes, but exhibits differences in scattering.

Figure 9A:
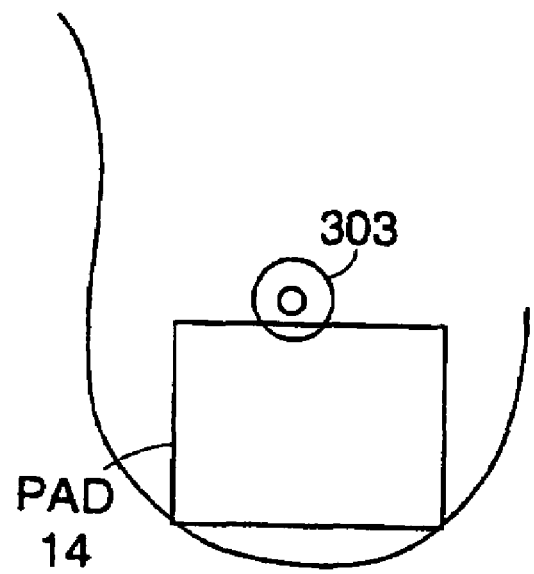
FIGS. 9A and 9B show respectively the left breast and the right breast during examination of a female patient lying supine face up, as shown in FIGS. 1B and 1C.
Figure 9B:
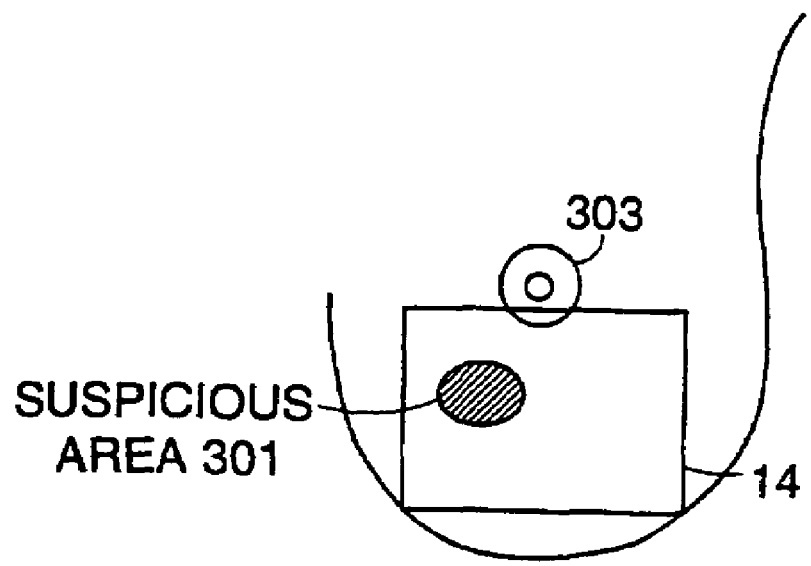
Figure 10A:
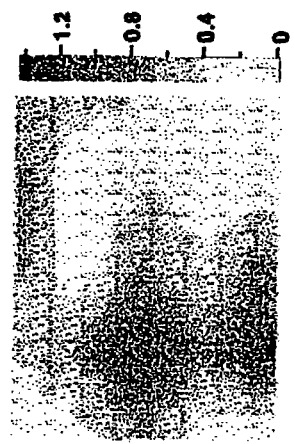
Figure 10B:
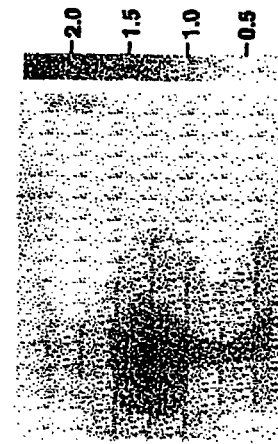
Figure 10C:
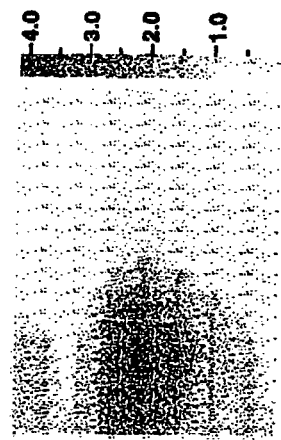
Figure 10D:
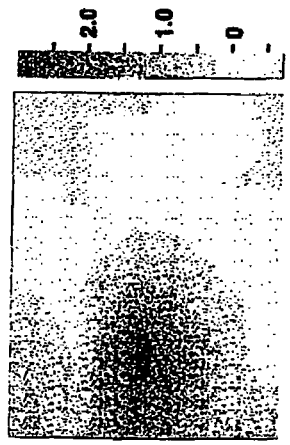

The following are examples of clinical data acquired by the amplitude cancellation system of FIG. 8 employing optical module 14. FIGS. 9A and 9B show respectively the left breast and the right breast during examination with a patient lying supine face up (i.e., the third position). The right breast (FIG. 9B) included a suspicious area 301 located below the nipple 303. FIGS. 10A through 10D are back-projection images collected by the amplitude cancellation system of FIG. 8 employing optical module 14 as shown in FIGS. 9A and 9B. FIGS. 10A and 10B are images of the right breast corrected for the model data at 750 nm and 830 nm, respectively. The x and y coordinates are in millimeters and the intensity in 0 V to 3 V with respect to the model. FIG. 10C is a blood deoxygenation image of the right breast corrected for the model data. FIG. 10D is a blood volume image of the right breast corrected for the model data FIGS. 11A and 11B are images of the right breast data minus the left breast data at 750 nm and 830 nm, respectively (No. 18). FIG. 11C is a blood deoxygenation image f the right breast data minus the left breast data. FIG. 11D is a blood volume image of the right breast minus the left breast data. These images have a high signal level and exhibit high congruence of the tumor.

FIGS. 12A through 12D show optical images of a patient who had a "suspicious area" identified below the nipple of the left breast by X-ray mammography. FIGS. 12A and 12B are images of the right breast data minus the left breast data at 750 nm and 830 nm, respectively. FIG. 12C is a blood deoxygenation image of the right breast data minus the left breast data. FIG. 12D is a blood volume image of the right breast minus the left breast data. FIGS. 12C and 12D exhibit only a blood volume increase of 0.18 V and a small negative value for deoxygenation of about 0.4. Therefore, these optical images would not be considered abnormal.

Figure 13A:
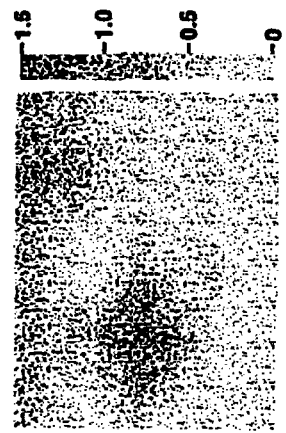
Figure 13B:
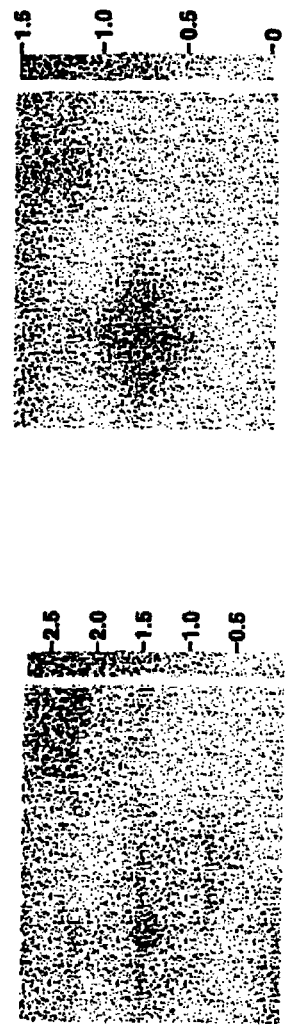
Figure 13C:
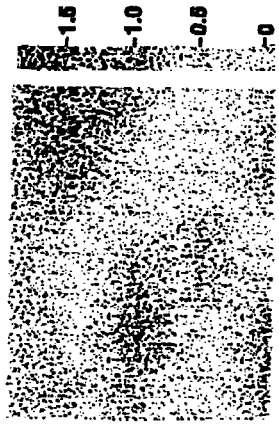
Figure 13D:
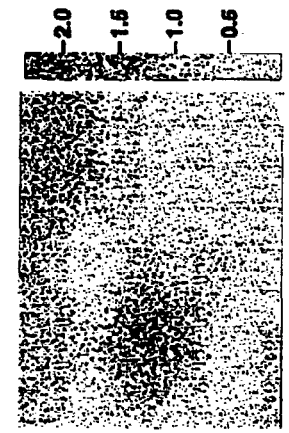

FIGS. 13A and 13B are images of the right breast corrected for the model data at 750 nm and 830 µm, respectively. FIG. 13C is a blood deoxygenation image of the right breast corrected for the model data. FIG. 13D is a blood volume image of the right breast corrected for the model data.

Discussion of the Images

Figure 14:
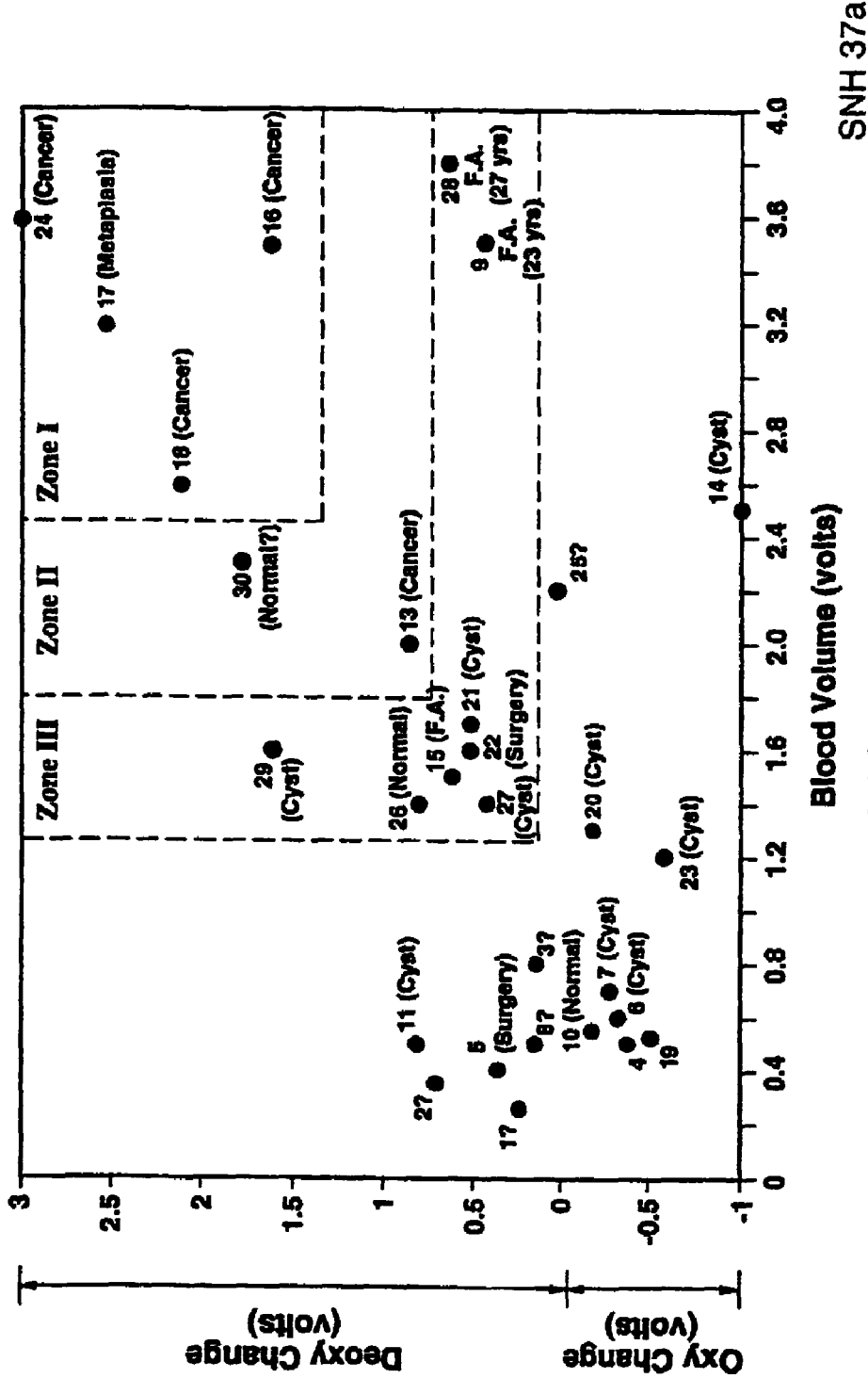
FIG. 14 is a two dimensional display of optical data from 30 studies of patients with suspicious masses.

FIG. 14 is a two dimensional plot of 30 studies of patients with suspicious masses based on mammographic data guidance provided as an example. Specifically, FIG. 14 displays angiogenicity and hypermetabolic activity of the measured masses as the blood volume increases and the deoxygenation increases. All patients had a palpable mass, and/or an X-ray mammography and/or ultrasound detected suspicious breast mass. Patients nos. 13, 16, 18 and 24 were identified as having a cancerous mass, while patients 17, 20, 25 and 28 had a significant risk of having a cancerous mass.

The two-dimensional nature of FIG. 14 permits the assignment of sensitivity and specificity according to the signal strength of blood volume data and the signal strength of deoxygenation data. I divided the region of signals in FIG. 14 into four zones. Zone I was defined for blood volume values above about 2.4 V and deoxygenation values above about 1.4 V. Zone II, located below Zone I, was defined for blood volume values above about 1.7 V and deoxygenation values above about 0.75 V. Zone III, located below Zone II, was defined for blood volume values above about 1.3 V and deoxygenation values above about 0.2 V. Zone IV was located below Zone III. In Zone I three out of four patients had a cancerous mass. In Zones III and II three out of five patients had a cancerous mass (not counting patient 30).

Bilateral Signals.

In these cases, bilateral congruence affords a diagnostic aid. In some cases, particularly in cancer bearing breast (point 13 (GR)), the left and right breast signals measured with respect to the model showed similar shapes and thus subtraction of the left and right mammographically dense breasts failed to give a recognizable object in the designated outer, lower portion of the left breast. While indeed a residual shape was seen at the bottom of the image, the region was not intense; the blood volume and the deoxygenation signals were about 0.9 and 0.4 V. However, when the model is used as a reference, the middle, left portion of the image gives signals 2 and 0.9 V. In this case, the signal is placed in Zone II in FIG. 14. However, a further study of such masses is desirable.

Subject No. 30 (likely normal) showed distinctive signals in the left portion of the right breast, but showed no distinctive signals in the region of the right breast, which was heterogeneous and dense. This subject (No. 30) showed no significant features in the data of the left breast minus model, but the data of the right breast minus model showed a clear anomaly in both blood volume and deoxygenation. This anomaly appeared on the data of the right breast on the inner side along the midline providing a highly significant signal from a congruent volumes. This subject was scored at 2.5 V and 1.9 V having heterogeneously dense breast (43 year old) but no mammographically detected tumor.

Studies Referenced to the Model Breast.

No. 25 (KS) was found to have a mass near the nipple, 9-11 o'clock in the left breast. Both breasts were characterized by significant blood volume and deoxygenation signals as if the breast had unusual glandular or active metabolic characteristics. However, there was a very clear spot at the mammographically indicated region in the deoxygenation image with respect to the models, but little signal in the congruent position in the blood volume minus model image. On subtraction two, there is poor congruence, again a small image in deoxygenation, and large non-congruent image at the mammographic indication. Thus, I scored the optical data of subject 25 against the model (i.e., the left breast minus model) because of background interference from the contralateral breast. Subject 15 lacks the optical data on the model, but a shape in the blood volume with no congruence in oxygenation was detected.

The optical images of subject 8 (LA) had a "suspicious mass" below the nipple in both left breast and right breast. In fact, there was rather good congruence between the left and right breasts in the blood volume images but the "oxygenation mass" was distant from the "suspicious mass". Thus, in the difference blood volume image the mass disappeared with no image left in the suspicious region.

A 23 year old subject (No. 9) showed a mammographically designated lower middle mass in the left breast. There is a congruent blood volume middle breast signal in both left and right breast showing a wide diffuse area of low intensity of deoxygenation in both breasts (about 1.8 V). The subject had similar anomalies in both breasts, with congruent deoxygenation. This subject was scored on the left breast only providing the values of about 1.8 and 0.5 V, respectively.

A 27 year old patient (No. 28) with fibroadenoma in the left breast near the midline displayed a very large blood volume signal of 3.8 V and a relatively small and diffuse deoxygenation signal with very poor congruence (0.7 V) placing the signal in Zone III.

Nipple Signal

In the contralateral (the right breast), the nipple shows as about a 1 cm shape in both the blood volume and deoxygenation images proving low signal levels of about 1 and 1.2 V, respectively (see FIGS. 13A through 13D).

Two Dimensional Charts

Figure 15A:
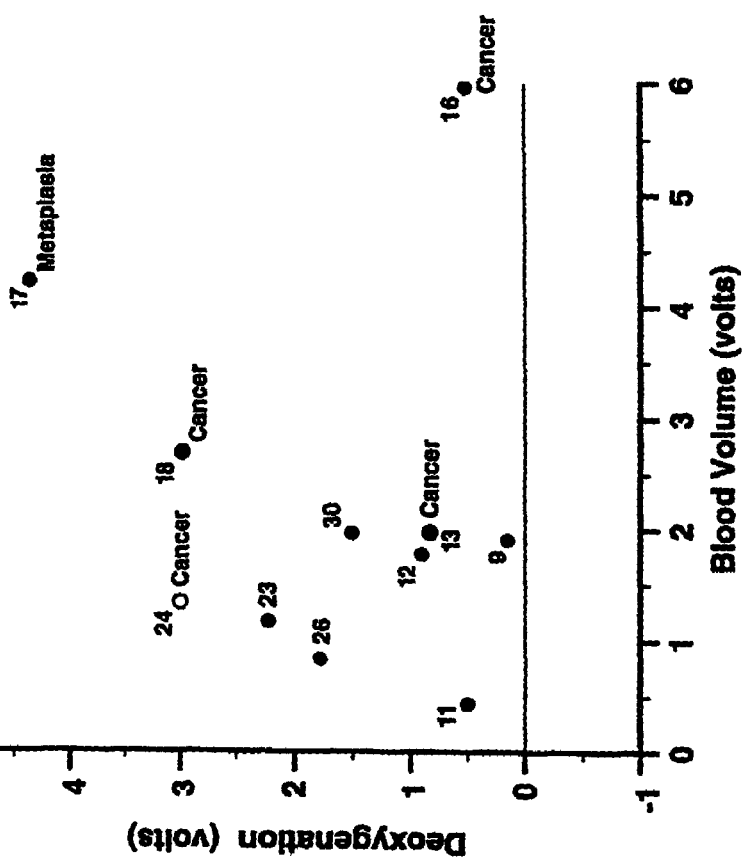
FIGS. 15 and 15A are a two dimensional displays of optical data shown in FIG. 14 using the contralateral breast data as a reference and using the breast model data as a reference, respectively.
Figure 15:
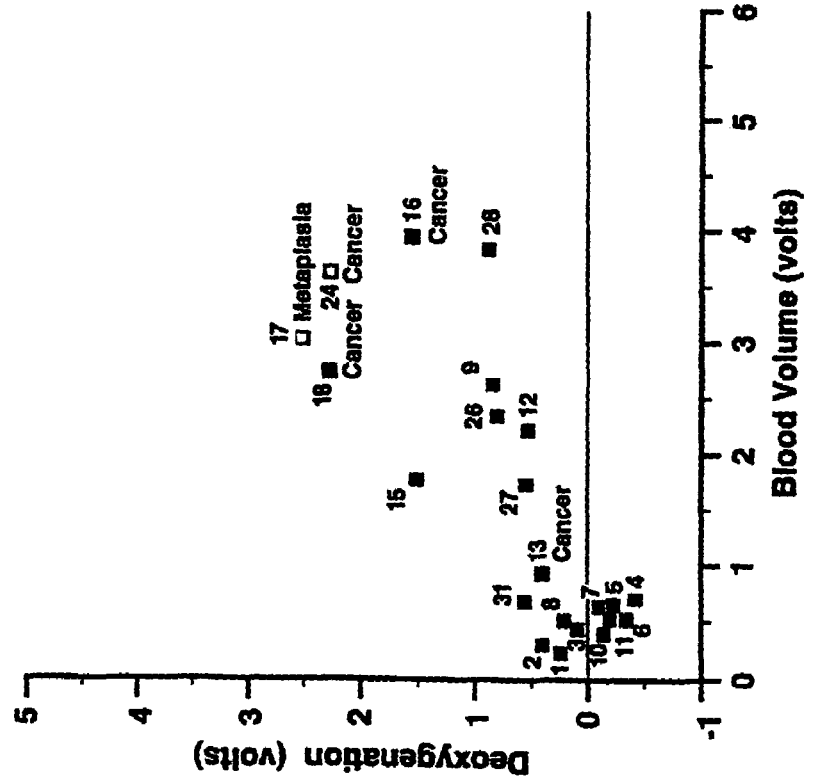

FIGS. 14 through 17 are provided to display and analyze the optical data. FIG. 14 displays the optical data evaluated based on mammographic data. FIG. 15 shows a chart of optical data displayed in FIG. 14 based upon "suspicious mass" guidance only, using the contralateral breast data as a reference. FIG. 15A shows a chart of optical data displayed in FIG. 14 based, however, upon "suspicious mass" guidance only, using the breast model data as a reference. The difference between FIG. 14 and FIGS. 15 and 15A is that in FIG. 14 the calculated data is based upon a given mammographic position. The blood volume and deoxygenation values are measured at a position closest to the mammographic position. On the other hand, in FIG. 15, the congruence of blood volume and oxygenation changes are used where ever it is observed in the breast. The use of the contralateral breast (i.e., the opposite breast) reduces the signals from the noncancerous tissue, but the measurement on the contralateral breast is not always feasible.

Figure 16A:
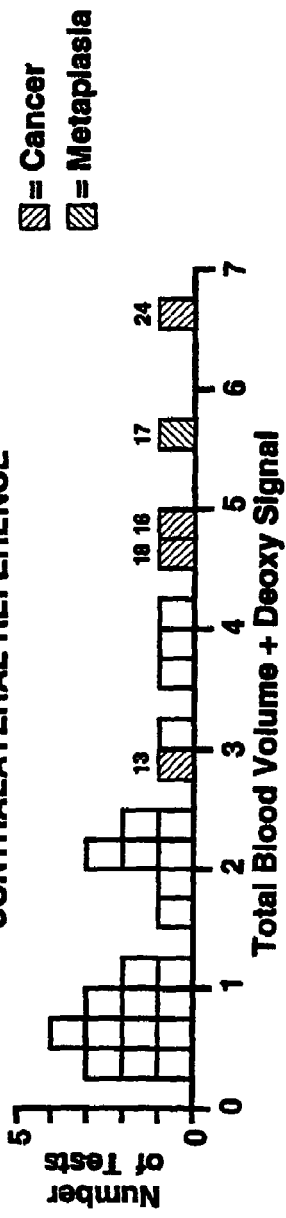
FIGS. 16A, 16B and 16C are histograms of data displayed in FIGS. 14, 15 and 15A, respectively.
Figure 16B:
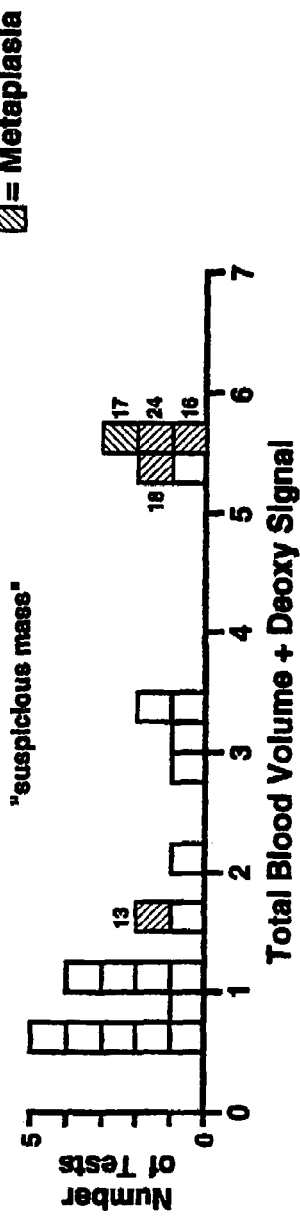
Figure 16C:
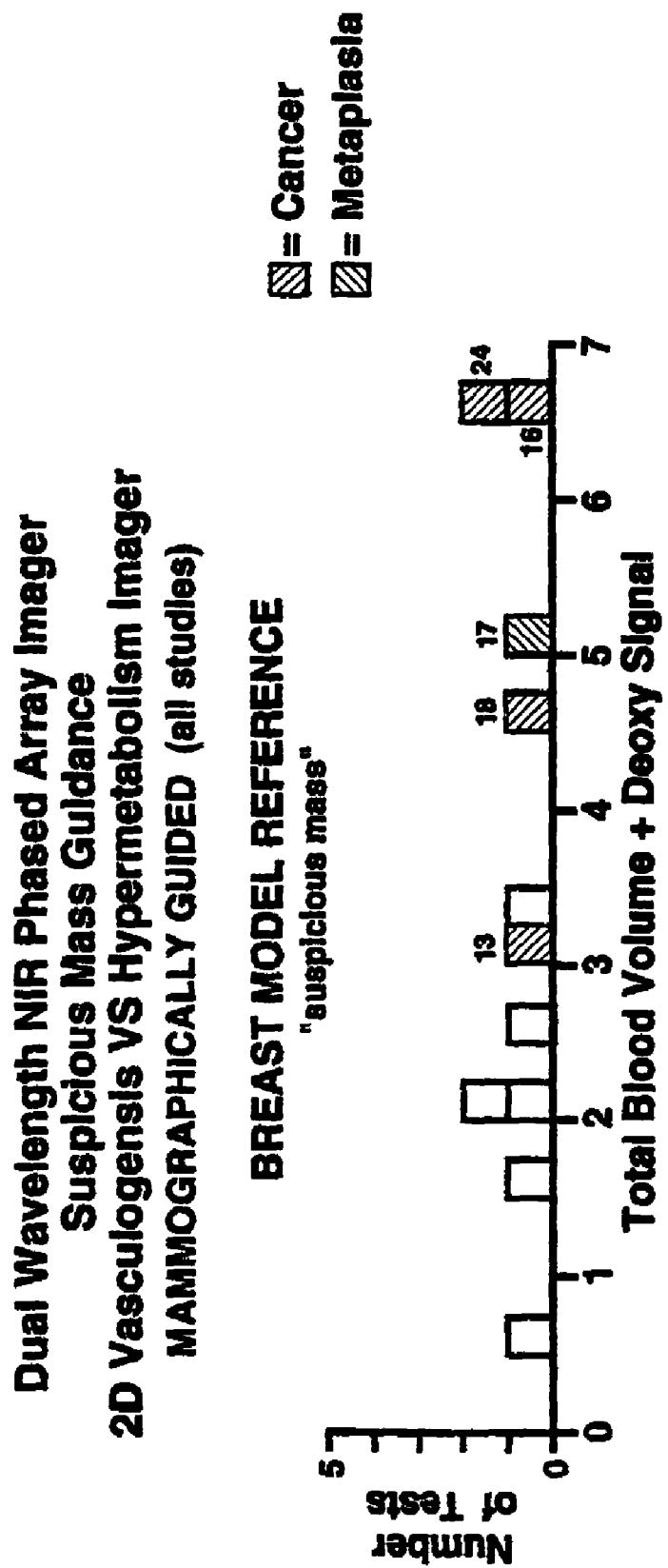

Histograms shown in FIGS. 16A, 16B, and 16C plot the optical data shown in FIGS. 14, 15 and 15A as a function of blood volume plus deoxygenation.

FIG. 16A uses all the mammographic information for guidance and contains five false positives and zero false negatives. In FIG. 16B, I use the contralateral breast as a reference, but maintained congruence of the blood volume image and the deoxygenation image. Here, the four cancers form a significant cluster, again in the upper right hand portion with the data from patient 17 (i.e., metaplasia) included. FIG. 16B shows an improved segregation above 4 volts. The use of the contralateral breast clusters the normal patients below signals 3.5 volts, and gives a large gap between 3.5 V and 5.2 V. Furthermore, it clusters cancerous data above 5.2 V with one false positive and one false negative. FIG. 16C shows the optical data referenced to the breast model. However, I note that in the display using the breast model, many studies failed the congruence test (FIG. 16C); specifically, only 11 out of 30 met the criteria. This suggests that the use of the congruence test adds to the specificity.

Quantitation of Co-Registration.

In principle, vasculogenesis (blood volume) and hypermetabolism (tissue hypoxia) occur in similar and often identical tissue locations. Therefore, I evaluated the congruence of the blood volume and deoxygenation images to further reinforce the identity of a suspicious mass. The following method for quantitation of the congruence was performed pixel by pixel. The first step was the normalization of the two images to equalize the maximum signals. A computer program was used to select the area and obtain the integrated value for the spatial congruence residual and for the blood volume signal. Then, subtraction pixel-by-pixel provided a residual value on which to base an estimate of the congruence of the two shapes, blood volume and deoxygenation. This was carried out for those shapes which appear by inspection to be congruent and the integral of the residual non-zero pixels is compared to the total signal. A simpler evaluation procedure can take the maximum value of the difference and divide it by the maximum value of the normalized value for the two images.

Figure 17:
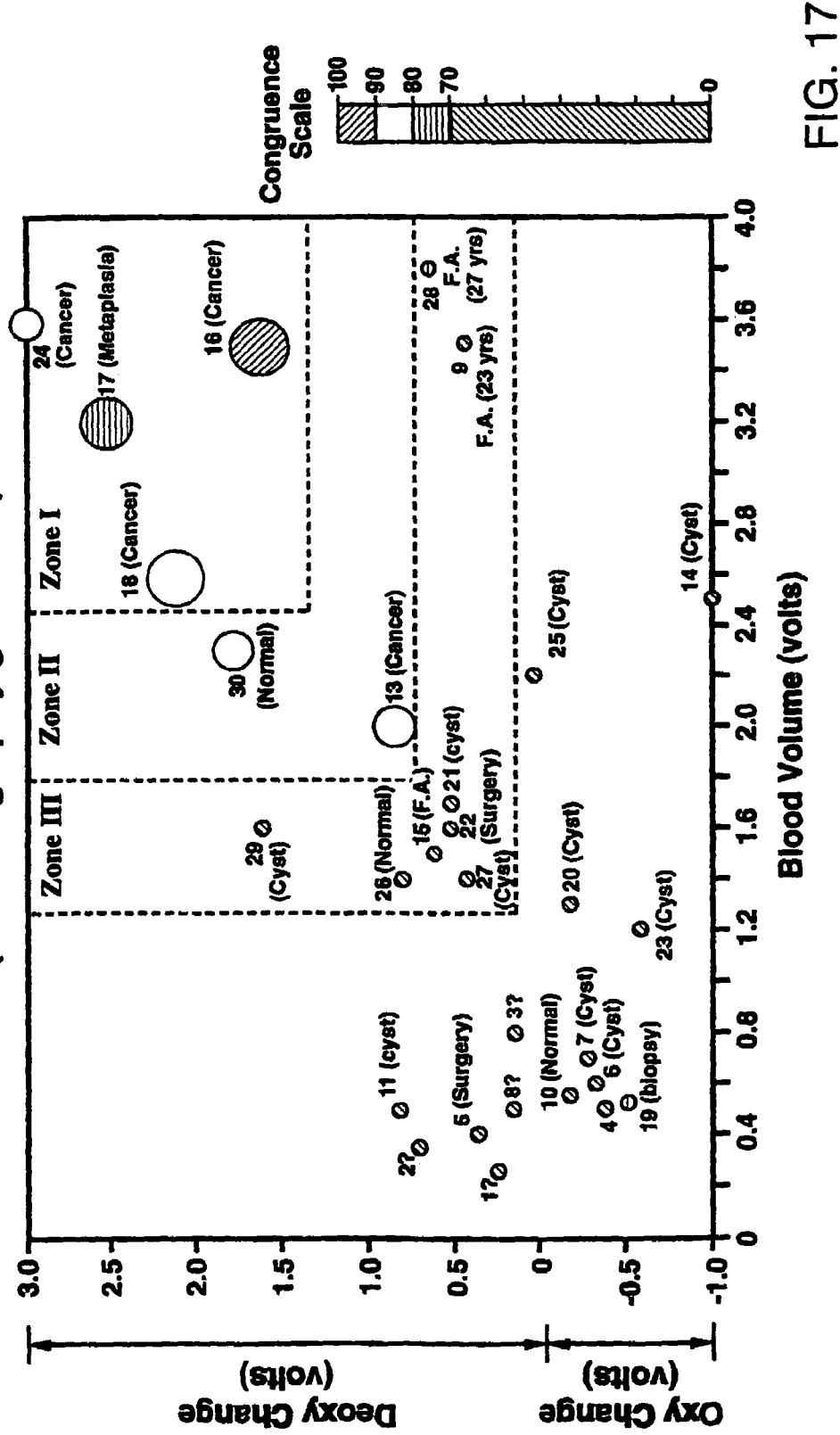
FIG. 17 is a "four" dimensional graph summarizing 30 studies of patients with suspicious masses.

The following test was applied to those images in the upper right region of FIG. 14. FIG. 17 is a "four" dimensional graph summarizing 30 studies of patients with suspicious masses. The blood volume (Volts) was plotted on the abscissa and deoxygenation (Volts) on the ordinate. The measured size of image was depicted as the circle diameter and the percentage congruence between the blood volume image and the deoxygenation image is shown by a color scale. The following is the color coding of the percentage of congruence signals given by a color scale in FIG. 17.

$$1 - \left(\frac{\text{maximum overlap residual}}{\text{maximum blood volume signal}}\right) \times 100$$

The diagram is summarized as follows:

1. The size of the image of a suspicious mass (plotted as one half its longest dimension).
2. The congruence of blood volumes and blood deoxygenation plotted in color.
3. The blood volume in the congruent region measured in Volts (scale of the abscissa).
4. Blood deoxygenation in the congruent region (scale of the ordinate).

For example, a red dot of a given size in the upper right hand quadrant of the diagram indicates a suspicious mass, having a large blood volume and a large deoxygenation with a high spatial congruence of the two parameters. Several measurements in this diagram either lacked congruence, lacked high blood volume, or lacked large blood deoxygenation. These are mainly in the lower left quadrant.

This preliminary study has employed a combination of angiogenesis and hypermetabolism as indices of tumor regenesis. While the study has been guided by mammographic/ultrasound location of the tumor volume, only in one case has that information been required to identify the site at which the optical measurements were to be taken, the resolution of the images of blood volume and deoxygenation is adequate to determine their congruence. The congruence level is at the >70% level for the images of cancer. Thus, morphology is an asset of these studies and a 2D projection of the tumor size is indicated by the images.

Localized increases of blood volume and of deoxygenation have been used as the principle criteria of this study, others may add to the sensitivity/specificity. The first one of these is an estimate of congruence which is over 80% for those studies in the upper right hand corner of the diagram and poor for those in the lower left sector. FIG. 17 indicates congruence of blood volume and deoxygenation with a color scale indicated on the margin of the figure. It is seen that the congruence is very high in cancer patients. Congruence is low elsewhere in the lower left corner and when it is less than 70% a blue color is used. The comparison of the non-congruent images is of interest, usually one feature or the other, blood volume or deoxygenation is well defined whilst the complementary feature is quite diffuse. A third parameter that can be added to the figure (and has been done in the case of the cancers) is half the size of the image in centimeters and most of the cancer bearing tissues areas are between 1 and 2 cm in diameter.

Breast Matching Medium

In other studies we have employed the breast immersed in a liquid of $\mu_a$, $\mu_s'$ approximately matching the tumor, intending to render it optically invisible except for the inhomogeneity introduced by the tumor. This has been found to be quite important when transmission measurements are made through the breast. In the above study, however, each patient was lying on her back placing the breast against the chest, the body wall and ribcage, which created a matching background for the optical radiation. In the case of fatty breasts, the soft tissue "runs" over the chest and forms a thinner and optically more acceptable system, where the suspicious mass may be much better detected than in pendant breasts. The lymphatics could also be studied by this method.

Higher Resolution Images

In previous studies, optical tomography has attempted to mimic the X-ray image by a 2D projection of absorbance usually in 2 planes as shown, for example, by Fantini, et al. using a compressed breast and transmission time or frequency domain methods. The success of this techniques is based upon the ability of the radiologist to identify the structures of either scattering or absorbing material that differ from the normal breast.

However, a high resolution is required to delineate such structural features on which mammographic identification of cancer is usually based, and high resolution is time intensive as well as apparatus intensive, i.e., numerous source detector combinations are required to achieve resolution comparable to PET/MRI. In this study, imaging resolution is employed mainly to increase the signal to noise ratio in quantifying optical properties of the tumor with respect to the normal, often adipose tissue.

In the above systems, imaging resolution is employed mainly to increase the signal to noise ratio in quantifying optical properties of the tumor with respect to normal tissue, or with trespect to a model of a normal tissue. However, the blood volume, oxygenation and deoxygenation data collected by the optical systems do not depend critically upon high resolution imaging.

An optical system with an increased number of sources and detectors will render higher spatial resolution. Furthermore, a larger source-detector separation (i.e., the input port to detection port separation) achieves deeper penetration of the introduced optical radiation. By using selected separation values, the above-described imaging systems can collect three-dimensional optical data that are used for three dimensional reconstruction.

Additional embodiments are within the following claims:

The invention claimed is:

1. An optical system for in vivo, non-invasive examination of breast tissue of a female subject comprising:
    at least one light source constructed to emit visible or infrared light and at least one light detector;
    an optical module including an array of optical input ports and detection ports located in a selected geometrical pattern to provide a multiplicity of photon migration paths inside an examined region of breast tissue, said optical input ports being constructed to introduce visible or infrared light emitted from said at least one light source, said optical detection ports being constructed to receive photons of light that have migrated in the examined tissue region from at least one of said input ports and provide said received light to said at least one light detector;
    a controller constructed and arranged to control operation of said at least one light source and said at least one light detector to detect light that has migrated over at least one of said photon migration paths; and
    a processor connected to receive signals from said at least one light detector and programmed to form at least two data sets, wherein each data value of said at least two data sets corresponds to said detected light for a pair of said input and said detection ports, a first of said data sets representing blood volume in the examined tissue region and a second of said data sets representing blood oxygenation in the examined tissue region; said processor being programmed to calculate spatial congruence of said first and second data sets by calculating a maximum value of a difference between said blood volume and oxygenation data divided by a maximum normalized value to detect abnormal tissue in the examined tissue region.

2. The optical system of claim 1 wherein said processor is programmed to form said second data set that includes hemoglobin deoxygenation values.

3. The optical system of claim 1 wherein said processor is programmed to form a third data set being collected by irradiation of a reference breast tissue region.

4. The optical system of claim 1 wherein said processor is programmed to order said first and second data sets as two-dimensional images and to determine said congruence using a formula:

$$1\left(\frac{\text{maximum overlap residual}}{\text{maximum selected tissue signal}}\right) \times 100.$$

5. The optical system of claim 4 wherein said processor is further programmed to determine a location of said abnormal tissue within the examined tissue region.

6. The optical system of claim 1 wherein said processor is programmed to produce from said data sets an image data set by implementing an optical tomography algorithm.

7. The optical system of claim 6 wherein said processor is programmed to implement said optical tomography algorithm employing factors related to determined probability distribution of photons attributable to the scattering character of the tissue being imaged.

8. The optical system of claim 6 further including a display device constructed to receive said image data set from said processor and to display an image.

9. The optical system of claim 1 wherein said controller is constructed and arranged to activate said at least one light source and said at least one light detector at a first selected distance between said input and detection ports and said processor is programmed to form said data sets for said first distance.

10. The optical system of claim 9 wherein said processor is programmed to produce an image data set from said data sets formed for said first distance.

11. The optical system of claim 9 wherein said controller is further constructed and arranged to activate said at least one light source and said at least one light detector at a second distance between said input and detection ports and said processor is programmed to form said data sets for said second distance.

12. The optical system of claim 1 further comprising
    a first oscillator constructed to generate a first carrier waveform at a first frequency on the order of $10^8$ Hz, said first frequency having a time characteristic compatible with the time delay of photon migration in the examined tissue region;
    said at least one light source being coupled to said first oscillator and constructed to generate said light modulated by said first carrier waveform;
    a phase detector constructed to determine change in a waveform of the detected light relative to the first carrier waveform of the introduced light and measure therefrom a phase shift of said detected light, said measured phase shift being indicative of scattering or absorptive properties of the examined tissue region; and
    said processor being programmed to form said data sets based on said measured phase shift.

13. The optical system of claim 12 further comprising
    a second oscillator constructed to generate a second waveform at a second frequency;
    said at least one light detector being a photomultiplier (PMT) arranged to receive a reference waveform at a reference frequency offset by a frequency on the order of $10^3$ Hz from said first frequency and to produce a signal, at said offset frequency, corresponding to said detected light; and
    said phase detector being adapted to compare, at said offset frequency, the detected light with the introduced light and to determine therefrom said phase shift.

14. The optical system of claim 1 further comprising:
    an oscillator constructed to generate a first carrier waveform of a selected frequency compatible with time delay of photon migration in the examined tissue region; said at least one light source being connected to receive from said oscillator said first carrier waveform and constructed to generate light modulated at said frequency;

a phase splitter connected to receive said first carrier waveform from said oscillator and produce first and second reference phase signals of predefined substantially different phases;

first and second double balanced mixers connected to receive from said phase splitter said first and second reference phase signals, respectively, and connected to receive from said at least one light detector said detector signals and to produce therefrom a in-phase output signal and a quadrature output signal, respectively; and said processor being connected to said double balanced mixers and arranged to receive said in-phase output signal and said quadrature output signal and programmed to form therefrom said data sets.

15. The optical system of claim 14 wherein said processor is programmed to calculate a phase shift ($\Theta_\lambda$) between said light introduced at said optical input ports and said light detected at said optical detection ports prior to forming said data sets.

16. The optical system of claim 14 wherein said processor is programmed to calculate an average migration pathlength of photons scattered in the examined tissue between said optical input ports and said optical detection ports prior to forming said data sets.

17. The optical system of claim 16 wherein said processor is programmed to employ further said pathlength in quantifying hemoglobin saturation (Y) of the examined tissue.

18. The optical system of claim 14 wherein said processor is programmed to calculate a signal amplitude ($A_\lambda$) determined as a square root of a sum of squares of said in-phase output signal and said quadrature output signal prior to forming said data sets.

19. The optical system of claim 18 further comprising:

a narrow band detector connected to receive from said at least one light detector said detector signals and to produce a DC output signal therefrom; and said processor is programmed to calculate a modulation index ($M_\lambda$) as a ratio of values of said signal amplitude and said signal amplitude plus said DC output signal.

20. The optical system of claim 1 further comprising:

at least one oscillator constructed to generate a carrier waveform of a selected frequency, said at least one light source being operatively connected to said oscillator constructed to generate light of a visible or infrared wavelength, said light being intensity modulated at said frequency to achieve a known light pattern;

said controller constructed to control the emitted light intensity or phase relationship of patterns simultaneously introduced from multiple input ports, said introduced patterns forming resulting light that possesses a substantial gradient of photon density in at least one direction, said resulting light being scattered and absorbed over said migration paths;

said at least one light detector constructed and arranged to detect over time the resulting light that has migrated in the tissue to said detection port, and said processor being further programmed to process signals of said detected resulting light in relation to said introduced light to create said data sets indicative of influence of the examined tissue upon said substantial gradient of photon density of said resulting light.

21. The optical system of claim 20 further comprising a phase detector constructed to detect a phase of the detected light and provide said phase to said processor.

22. The optical system of claim 20 further comprising an amplitude detector constructed to detect an amplitude of the detected light and provide said amplitude to said processor.

23. The optical system of claim 20 wherein the phase relationship of light patterns introduced from two input ports is 180 degrees.

24. The optical system of claim 1 wherein said at least one light source produces relatively long light pulses and the processor is programmed to form said data sets by subtracting amplitude of two said pulses emitted from two input ports located symmetrically relative to one detection port.

25. The optical system of claim 1, wherein said at least one light source is constructed to emit photons of two wavelengths selected to provide sensitivity to a tissue constituent.

26. The optical system of claim 1 wherein said at least one light source is constructed to emit photons of two wavelengths providing sensitivity to a tissue constituent including an endogenous pigment.

27. The optical system of claim 1 wherein said at least one light source is constructed to emit photons of two wavelengths providing sensitivity to an endogenous pigment including hemoglobin.

28. The optical system of claim 1 wherein said at least one light source is constructed to emit photons of two wavelengths providing sensitivity to a tissue constituent including an exogenous pigment.

29. The optical system of claim 1 wherein said at least one light source is constructed to emit photons of two wavelengths providing sensitivity to an exogenous pigment including a selected contrast agent.

30. The optical system of claim 1, wherein said at least one light source includes a multiplicity of light sources embedded in said optical module and said at least one light detector includes a multiplicity of light detectors embedded in said optical module.

31. The optical system of claim 1, wherein said optical module includes several said detection ports equally spaced apart from each of said input ports.

32. The optical system of claim 1, wherein said optical module includes several said input ports equally spaced apart from each of said detection ports.

33. An optical system for in vivo, non-invasive examination of breast tissue of a female subject comprising:

at least one light source constructed to emit visible or infrared light and at least one light detector;

an optical module including an array of optical input ports and detection ports located in a selected geometrical pattern to provide a multiplicity of photon migration paths inside an examined region of breast tissue, said optical input ports being constructed to introduce visible or infrared light emitted from said at least one light source, said optical detection ports being constructed to receive photons of light that have migrated in the tissue from at least one of said input ports and provide said received light to said at least one light detector;

a controller constructed and arranged to control operation of said at least one light source and said at least one light detector to detect light that has migrated over at least one of said photon migration paths; and a processor connected to receive signals from said at least one light detector and programmed to form at least two data sets, wherein each data value of said at least two data sets corresponds to said detected light for a pair of said input and said detection ports, a first of said data sets being collected by irradiating said examined tissue region of interest and a second of said data sets being collected by irradiating a reference tissue region having similar light scattering and absorptive properties as the examined tissue region for normal tissue, said processor being programmed to calculate spatial congruence of said first and second data sets by calculating a maximum value of a difference between said first of said data sets and said second of said data sets divided by a maximum normalized value to detect abnormal tissue in the examined tissue region.

34. The optical system of claim 33 wherein said processor is further programmed to calculate blood volume values for said first data set and said second data set and arranged to calculate said congruence for said blood volume values.

35. The optical system of claim 33 wherein said processor is further programmed arranged to calculate oxygenation values for said first data set and said second data set and is arranged to calculate said congruence for said oxygenation values.

36. The optical system of claim 33 wherein said at least one light source produces relatively long light pulses and the processor is programmed to form said data sets by subtracting amplitude of two said pulses emitted from two input ports located symmetrically relative to one detection port.

37. The optical system of claim 33, wherein said at least one light source is constructed to emit photons of two wavelengths selected to provide sensitivity to a tissue constituent.

38. The optical system of claim 33 wherein said at least one light source is constructed to emit photons of two wavelengths providing sensitivity to an endogenous pigment.

39. The optical system of claim 33 wherein said at least one light source is constructed to emit photons of two wavelengths providing sensitivity to an endogenous pigment including hemoglobin.

40. The optical system of claim 33 wherein said at least one light source is constructed to emit photons of two wavelengths providing sensitivity to an exogenous pigment.

41. The optical system of claim 33 wherein said at least one light source is constructed to emit photons of two wavelengths providing sensitivity to an exogenous pigment including a selected contrast agent.

42. The optical system of claim 33, wherein said at least one light source includes a multiplicity of light sources embedded in said optical module and said at least one light detector includes a multiplicity of light detectors embedded in said optical module.

43. The optical system of claim 33, wherein said optical module includes several said detection ports equally spaced apart from of each said input ports.

44. The optical system of claim 33, wherein said optical module includes several said input ports equally spaced apart from each of said detection ports.

45. An optical method for in viva, non-invasive examination of breast tissue of a female subject comprising:

providing an optical module including an array of optical input ports and detection ports located in a selected geometrical pattern to provide a multiplicity of photon migration paths inside an examined region of breast tissue;

placing said optical module on the breast of a female subject;

introducing visible or infrared light from at least one of said optical input ports into the examined tissue region and receiving photons of light that have migrated in the examined tissue region to at least one of said detection ports;

detecting said received photons by at least one light detector optically coupled to said at least one detection port;

controlling said introducing and detecting steps to collect optical data corresponding to photons of light that have migrated between selected input and detection ports;

processing said optical data to form at least two data sets, a first of said data sets representing blood volume in the examined tissue region and a second of said data sets representing blood oxygenation in the examined tissue region; and calculating spatial congruence of said first and second data sets by calculating a maximum value of a difference between said blood volume and oxygenation data divided by a maximum normalized value to detect abnormal tissue in the examined tissue region.

46. The method of claim 45 wherein the female subject is lying supine face upward having her breast spread over her chest.

47. The method of claim 45 further including ordering said first and second data sets as two-dimensional images and determining said congruence using said two-dimensional images.

48. The method of claim 45 further including ordering said first and second data sets as two-dimensional images and determining said congruence using a formula:

$$1\left(\frac{\text{maximum overlap residual}}{\text{maximum selected tissue signal}}\right) \times 100.$$

49. The method of claim 48 further including determining a location of said abnormal tissue within the examined tissue region.

50. The method of claim 45 wherein said processing includes producing from said data sets an image data set by implementing an optical tomography algorithm.

51. The method of claim 50 in which said optical tomography algorithm employs factors related to determined probability distribution of photons attributable to the scattering character of the tissue being imaged.

52. The method of claim 50 further including displaying said image data set.

* * * * *